(12) United States Patent
Puttaraju et al.

(10) Patent No.: US 8,053,232 B2
(45) Date of Patent: *Nov. 8, 2011

(54) CORRECTION OF ALPHA-1-ANTITRYPSIN GENETIC DEFECTS USING SPLICEOSOME MEDIATED RNA TRANS SPLICING

(75) Inventors: Madaiah Puttaraju, Germantown, MD (US); Edward Otto, Reston, VA (US); Mariano A. Garcia-Blanco, Durham, NC (US); Gerard J. McGarrity, Gaithersburgh, MD (US); Gary F. Temple, Washington Grove, MD (US); Lloyd G. Mitchell, Bethesda, MD (US); Colette Cote, Gaithersburgh, MD (US); S. Gary Mansfield, Montgomery Village, MD (US)

(73) Assignee: VIRxSYS Corporation, Gaithersburg, MD (US)

( * ) Notice: Subject to any disclaimer, the term of this patent is extended or adjusted under 35 U.S.C. 154(b) by 593 days.

This patent is subject to a terminal disclaimer.

(21) Appl. No.: 11/040,634

(22) Filed: Jan. 21, 2005

(65) Prior Publication Data

US 2006/0234247 A1  Oct. 19, 2006

Related U.S. Application Data

(60) Provisional application No. 60/538,797, filed on Jan. 23, 2004.

(51) Int. Cl.
*C12N 5/00* (2006.01)
*C12N 15/12* (2006.01)
*C12N 15/63* (2006.01)
*C12N 15/86* (2006.01)

(52) U.S. Cl. ..................... 435/325; 435/320.1
(58) Field of Classification Search .......... None
See application file for complete search history.

(56) References Cited

U.S. PATENT DOCUMENTS

| | | | |
|---|---|---|---|
| 4,946,778 A | 8/1990 | Ladner et al. ............... 435/69.6 | |
| 4,980,286 A | 12/1990 | Morgan et al. | |
| 4,981,783 A | 1/1991 | Augenlicht ............... 435/6 | |
| 5,354,678 A | 10/1994 | Lebkowski et al. | |
| 5,585,362 A | 12/1996 | Wilson et al. | |
| 5,589,377 A | 12/1996 | Lebkowski et al. | |
| 5,599,672 A | 2/1997 | Liang et al. ............... 435/6 | |
| 5,616,326 A | 4/1997 | Spibey | |
| 5,670,488 A | 9/1997 | Gregory et al. | |
| 5,700,470 A | 12/1997 | Saito et al. | |
| 5,731,172 A | 3/1998 | Saito et al. | |
| 5,747,072 A | 5/1998 | Davidson et al. | |
| 5,756,283 A | 5/1998 | Wilson et al. | |
| 5,789,390 A | 8/1998 | Descamps et al. | |
| 5,820,868 A | 10/1998 | Mittal et al. | |
| 5,837,484 A | 11/1998 | Trempe et al. | |
| 5,843,742 A | 12/1998 | Natsoulis et al. | |
| 5,851,806 A | 12/1998 | Kovesdi et al. | |
| 5,858,351 A | 1/1999 | Podsakoff et al. | |
| 5,869,037 A | 2/1999 | Crystal et al. | |
| 5,871,982 A | 2/1999 | Wilson et al. | |
| 5,877,011 A | 3/1999 | Armentano et al. | |
| 5,882,874 A | 3/1999 | Fisher | |
| 5,885,808 A | 3/1999 | Spooner et al. | |
| 5,891,690 A | 4/1999 | Massie | |
| 5,919,676 A | 7/1999 | Graham et al. | |
| 5,922,576 A | 7/1999 | He et al. | |
| 5,928,944 A | 7/1999 | Seth et al. | |
| 5,932,210 A | 8/1999 | Gregory et al. | |
| 5,952,221 A | 9/1999 | Kurtzman et al. | |
| 5,962,311 A | 10/1999 | Wickham et al. | |
| 5,962,313 A | 10/1999 | Podsakoff et al. | |
| 5,998,205 A | 12/1999 | Hallenbeck et al. | |
| 6,013,487 A | 1/2000 | Mitchell | |
| 6,025,192 A | 2/2000 | Beach et al. ............... | 435/320.1 |
| 6,083,702 A | 7/2000 | Mitchell et al. | |
| 6,146,877 A | 11/2000 | Fisher | |

(Continued)

FOREIGN PATENT DOCUMENTS

WO   WO 88/09810   12/1988

(Continued)

OTHER PUBLICATIONS

Scheidner, G. et al., "Genomic DNA transfer with a high-capacity adenovirus vector results in improved in vivo gene expression and decreased toxicity", 1998, Nat. Genetics, vol. 18: pp. 180-183.*
Stoll, S. et al., "Epstein-Barr Virus/Human Vectors Provides High-Level, Long-Term Expression of alpha1-Antitrypsin in Mice", 2001, Mol. Ther., vol. 4: pp. 122-129.*
Elbashir, S. et al., "RNA interference is mediated by 21 and 22 nucleotide RNAs", 2001, Genes & Dev., vol. 15: pp. 188-200.*
Crystal, R., "Alpha1-Antitrypsin Deficincy, Emphysema, and Liver disease", 1990, J. Clin. Invest., vol. 85: pp. 1343-1352.*
U.S. Appl. No. 09/648,310, filed Aug. 25, 2000, Fisher et al.
United States Patent Publication 2001/0014734 by Fisher published Aug. 16, 2001 and entitled "Progression elevated gene-3 and uses thereof."
Rubanyi G.M. The future of human gene therapy Mol Aspects of Medicine 2001 22:113-142.
Peng XY, Won JH, Rutherford T, Fujii T, Zelterman D, Pizzorno G, Sapi E, Leavitt J, Kacinski B, Crystal R, Schwartz P, Deisseroth A. The use of the L-plastin promoter for adenoviral-mediated, tumor-specific gene expression in ovarian and bladder cancer cell lines. Cancer Res 2001;61(11):4405-4413.

(Continued)

*Primary Examiner* — Michael Burkhart
(74) *Attorney, Agent, or Firm* — VIRxSYS Corporation; Serge Sira, Esq.

(57) ABSTRACT

The present invention provides methods and compositions for generating novel nucleic acid molecules through targeted spliceosomal mediated RNA trans-splicing. The compositions of the invention include pre-trans-splicing molecules (PTMs) designed to interact with a SERPINA1 target precursor messenger RNA molecule (target pre-mRNA) and mediate a trans-splicing reaction resulting in the generation of a novel chimeric RNA molecule (chimeric RNA). In particular, the PTMs of the present invention include those genetically engineered to interact with SERPINA1 target pre-mRNA so as to result in correction of SERPINA1 genetic defects responsible for AAT deficiency. The PTMs of the invention may also comprise sequences that are processed out of the PTM to yield duplex siRNA molecules directed specifically to mutant SERPIN A1 mRNAs. Such duplexed siRNAs are designed to reduce the accumulation of toxic AAT protein in liver cells. The methods and compositions of the present invention can be used in gene therapy for correction of SERPINA1 disorders such as AAT deficiency.

24 Claims, 9 Drawing Sheets

U.S. PATENT DOCUMENTS

| | | | |
|---|---|---|---|
| 6,235,310 B1 | 5/2001 | Wang et al. | 424/450 |
| 6,245,520 B1 | 6/2001 | Wang et al. | 435/6 |
| 6,245,747 B1 | 6/2001 | Porter et al. | 514/44 |
| 6,255,071 B1 | 7/2001 | Beach et al. | 435/69.1 |
| 6,280,978 B1 | 8/2001 | Mitchell et al. | |
| 7,094,399 B2 | 8/2006 | Otto | |
| 7,399,753 B2 | 7/2008 | Mitchell | |
| 2006/0094110 A1 | 5/2006 | McGarrity | |
| 2006/0134658 A1 | 6/2006 | Garcia-Blanco | |
| 2006/0154257 A1 | 7/2006 | Mitchell | |
| 2006/0160182 A1 | 7/2006 | McGarrity | |
| 2006/0172381 A1 | 8/2006 | McGarrity | |
| 2006/0177933 A1 | 8/2006 | Puttaraju | |
| 2006/0194317 A1 | 8/2006 | Puttaraju | |
| 2006/0246422 A1 | 11/2006 | Mitchell | |

FOREIGN PATENT DOCUMENTS

| | | |
|---|---|---|
| WO | WO 89/10134 | 11/1989 |
| WO | WO 89/12690 | 12/1989 |
| WO | WO 98/11241 | 3/1998 |
| WO | WO 98/42315 | 10/1998 |
| WO | WO 99/43844 | 9/1999 |
| WO | WO 99/49898 | 10/1999 |
| WO | WO 00/09734 | 2/2000 |
| WO | WO 00/09734 | 3/2000 |
| WO | WO 00/55174 | 9/2000 |
| WO | WO 00/58350 | 10/2000 |
| WO | WO 01/46386 | 6/2001 |
| WO | WO 02/08242 | 1/2002 |
| WO | WO 02/16419 | 2/2002 |

OTHER PUBLICATIONS

Perrais M, Pigny P, Ducourouble MP, Petitprez D, Porchet N, Aubert JP, Van Seuningen I. Characterization of human mucin gene MUC4 promoter: importance of growth factors and proinflammatory cytokines for its regulation in pancreatic cancer cells. J Biol Chem 2001;276(33):30923-30933.

Su Z, Shi Y, Fisher PB. Rattus norvegicus progression elevated gene-3 protein (Peg-3) gene, promoter region. Genbank Accession No. AF351130. Submitted Feb. 20, 2001.

Tanaka M, Inase N, Miyake S, Yoshizawa Y. Neuron specific enolase promoter for suicide gene therapy in small cell lung carcinoma. Anticancer Res 2001;21(1A):291-194.

Xie X, Zhao X, Liu Y, Young CY, Tindall DJ, Slawin KM, Spencer KM. Robust prostate-specific expression for targeted gene therapy based on the human kallikrein 2 promoter. Hum Gene Ther 2001;12(5):549-561.

Adachi Y, Reynolds PN, Yamamoto M, Grizzle WE, Overturf K, Matsubara S, Muramatsu T, Curiel DT. Midkine promoter-based adenoviral vector gene delivery for pediatric solid tumors. Cancer Res 2000;60(16):4305-4310.

Curran MA, Kaiser SM, Achacoso PL, Nolan GP. Efficient transduction of nondividing cells by optimized feline immunodeficiency virus vectors. Mol Ther 2000;1(1):31-38.

U.S. Appl. No. 09/648,310 by Fisher et al., filed Aug. 25, 2000, and entitled "Progression suppressed gene 13 (PSGen13) and uses thereof."

Hu, R.-M et al., Gene expression profiling in the human hypothalamus-pituitary-adrenal axis and full-length cDNA cloning Proc Natl Acad Sci USA 2000 97(17):9543-9548.

Inase N, Horita K, Tanaka M, Miyake S, Ichioka M, Yoshizawa Y. Use of gastrin-releasing peptide promoter for specific expression of thymidine kinase gene in small-cell lung carcinoma cells. Intl J Cancer 2000;85(5):716-719.

O'Keefe et al., Prostate-specific suicide gene therapy using the prostate-specific membrane antigen promoter and enhancer. Prostate 2000;45(2):149-157.

Perrais M, Pigny P, Ducourouble MP, Petitprez D, Porchet N, Aubert JP, Van Seuningen I. *Homo sapiens* mucin 4 (MUC4) gene, promoter sequence and partial cds. GenBank Accession No. AF241535. Submitted Mar. 3, 2000.

Ye et al., "*Homo sapiens* HSP C280 mRNA, Partial CDS; Human partial CDS from stem cells," EMBL #AF161398, Feb. 1, 2000.

Zhang Q.-H et al., Cloning and functional analysis of cDNAs with open reading frames for 300 previously undefined genes expressed in CD34+ hematopoietic stem/progenitor cells Genome Res 2000 10:1546-1560.

Case SA, Price MA, Jordan CT, Yu XJ, Wang L, Bauer G, Haas DL, Xu D, Stripecke R, Naldini L, Kohn DB, Crooks GM. Stable transduction of quiescent CD34(+)CD38(−) human hematopoietic cells by HIV-1-based lentiviral vectors. Proc Natl Acad Sci USA 1999;96(6):2988-2993.

Connelly S. Adenoviral vectors for liver-directed gene therapy. Curr Opin Mol Ther 1999;1(5):565-572.

Gopalkrishnan RV, Christiansen KA, Goldstein NI, DePinho RA, Fisher PB. Use of the human EF-1alpha promoter for expression can significantly increase success in establishing stable cell lines with consistent expression: a study using the tetracycline-inducible system in human cancer cells. Nucl Acids Res 1999;27:4775-4782.

Han Z.-g et al., Molecular cloning of six novel Kruppel-like zinc finger genes from hematopoietic cells and identification of a novel transregulatory domain KRNB J Biol Chem 1999 274(50): 35741-35748.

Katabi MM, Chan HL, Karp SE, Batist G. Hexokinase type II: a novel tumor specific promoter for gene-targeted therapy differentially expressed and regulated in human cancer cells. Hum Gene Ther 1999;10(2):155-164.

Pan CX, Koeneman KS. A novel tumor-specific gene therapy for bladder cancer. Med Hypotheses 1999;53(2):130-135.

Polo JM, Belli BA, Driver DA, Frolov I, Sherrill S, Hariharan MJ, Townsend K, Perri S, Mento SJ, Jolly DJ, Chang SM, Schlesinger S, Dubensky TW Jr. Stable alphavirus packaging cell lines for Sindbis virus and Semliki Forest virus-derived vectors. Proc Natl Acad Sci USA 1999;96(8):4598-4603.

Shridhar V, Staub J, Huntley B, Cliby W, Jenkins R, Pass HI, Hartmann L, Smith DI. A novel region of deletion on chromosome 6q23.3 spanning less than 500 Kb in high grade invasive epithelial ovarian cancer. Oncogene Jul. 1, 1999;18(26):3913-3918.

Stackhouse MA, Buchsbaum DJ, Kancharla SR, Grizzle WE, Grimes C, Laffoon K, Pederson LC, Curiel DT. Specific membrane receptor gene expression targeted with radiolabeled peptide employing the erbB-2 and DF3 promoter elements in adenoviral vectors. Cancer Gene Ther 1999;6(3):209-219.

Su ZZ, Goldstein NI, Jiang H, Wang MN, Duigou GJ, Young CS, Fisher PB. PEG-3, a nontransforming cancer progression gene, is a positive regulator of cancer aggressiveness and angiogenesis. Proc Natl Acad Sci USA 1999;96(26):15115-15120.

Ye et al., *Homo sapiens* HSPC280 mRNA. GenBank Accession No. AF161398. May 14, 1999.

Zhang WW. Development and application of adenoviral vectors for gene therapy of cancer. Cancer Gene Ther 1999;6(2):113-138.

Fisher, PSGen13. dbEST ID No. 1903240. GenBank Accession No. AI144570. Nov. 23, 1998.

Kang DC, LaFrance R, Su ZZ, Fisher PB. Reciprocal subtraction differential RNA display: an efficient and rapid procedure for isolating differentially expressed gene sequences. Proc Natl Acad Sci USA 1998;95(23):13788-13793.

Lee et al., 1998, GenBank Acc. No. AA891725.

Olsen JC. Gene transfer vectors derived from equine infectious anemia virus. Gene Ther 1998;5(11):1481-1487.

Winkles JA. Serum-and polypeptide growth factor-inducible gene expression in mouse fibroblasts. Prog Nucleic Acids Res Mol Biol 1998;58:41-78.

Zhang Qh, Yu Y, Zhang S, Wei H, Zhou G, Ouyanfg S, Luo L, Bi J, Liu M, He F (1998). *Homo sapiens* PRO2013 mRNA. GenBank Accession No. AF116682. Dec. 24, 1998.

Friedmann T., Overcoming the Obstacles to Gene Therapy Scientific American Jun. 1997 96-101.

Gura et al., Systems for identifying new drugs are often faulty. Science 1997; 278:1041-1042.

Hartwell et al., Integrating Genetic Approaches into the Discovery of Anticancer Drugs. Science 1997; 278:1064-1068.

Sagerström CG, Sun BI, Sive HL. Subtractive cloning: past, present, and future. Annu Rev Biochem 1997;66:751-783.

Strausberg R. Hypothetical 18.3 kDa Protein. dbEST ID No. 3155305. EST wu69a04.x1. Image Clone ID No. 2525262. GenBank Accession No. AW024795. Submitted 1997.

Su ZZ, Shi Y, Fisher PB. Subtraction hybridization identifies a transformation progression-associated gene PEG-3 with sequence homology to a growth arrest and DNA damage-inducible gene. Proc Natl Acad Sci USA 1997;94(17):9125-9130.

Takakuwa K, Fujita K, Kikuchi A, Sugaya S, Yahata T, Aida H, Kurabayashi T, Hasegawa I, Tanaka K. Direct intratumoral gene transfer of the herpes simplex virus thymidine kinase gene with DNA-liposome complexes: growth inhibition of tumors and lack of localization in normal tissues. Jpn J Cancer Res 1997;88(2):166-175.
Verma I.M. et al Gene therapy-promises, problems and prospects Nature 1997 389:239-242.
Wong B, Park CG, Choi Y. Identifying the molecular control of T-cell death; on the hunt for killer genes. Semin Immunol 1997;9(1):7-16.
Zhang L, Zhou W, Velculescu VE, Kern SE, Hruban RH, Hamilton SR, Vogelstein B, Kinzler KW. Gene expression profiles in normal and cancer cells. Science 1997;276(5316):1268-1272.
Boyce FM, Bucher NL. Baculovirus-mediated gene transfer into mammalian cells. Proc Natl Acad Sci U S A 1996;93(6):2348-2352.
Jiang H, Su ZZ, Lin JJ, Goldstein NI, Young CS, Fisher PB. The melanoma differentiation associated gene mda-7 suppresses cancer cell growth. Proc Natl Acad Sci USA 1996;93(17):9160-9165.
Lan Ms. Kesh: , Kanai F, Shiratori Y, Okabe S, Yoshida Y, Wakimoto H, Hamada H, Tanaka T, Ohashi M, Omata M. Tumor-specific gene expression in carcinoembryonic antigen-producing gastric cancer cells using adenovirus vectors. Gastroenterology 1996;111(5):1241-1251.
Strayer DS, Milano J. SV40 mediates stable gene transfer in vivo. Gene Ther 1996;3(7):581-587.
Wan JS, Sharp SJ, Poirier GM, Wagaman PC, Chambers J, Pyati J, Horn YL, Galindo JE, Huvar A, Peterson PA, Jackson MR, Erlander MG. Cloning differentially expressed mRNAs. Nat Biotechnol 1996;14(13):1685-1691.
Debouck C. Differential display or differential dismay? Curr. Opin. Biotechnol 1995;6:597-599.
Ido A, Nakata K, Kato Y, Nakao K, Murata K, Fujita M, Ishii N, Tamaoki T, Shiku H, Nagataki S. Gene therapy for hepatoma cells using a retrovirus vector carrying herpes simplex virus thymidine kinase gene under the control of human alpha-fetoprotein gene promoter. Cancer Res 1995;55(14):3105-3109.
Jiang H, Lin JJ, Su ZZ, Goldstein NI, Fisher PB. Subtraction hybridization identifies a novel melanoma differentiation associated gene, mda-7, modulated during human melanoma differentiation, growth and progression. Oncogene 1995;11(12):2477-2486.
Jiang H, Lin J, Su ZZ, Herlyn M, Kerbel RS, Weissman BE, Welch DR, Fisher PB. The melanoma differentiation-association gene mda-6, which encodes the cyclin-dependent kinase inhibitor p21, is differentially expressed during growth, differentiation and progression in human melanoma cells. Oncogene 1995;10(9):1855-1864.
Lee NH. EST111677 derived from NGF-treated rat PC-12 cells. dbEST ID No. 295231. GenBank Accession No. H34607. Submitted Jul. 19, 1995.
Maser RL, Calvet JP. Analysis of differential gene expression in the kidney by differential cDNA screening, subtractive cloning, and mRNA differential display. Semin Nephrol 1995;15(1):29-42.
McClelland M, Mathieu-Daude F, Welsh J. RNA fingerprinting and differential display using arbitrarily primed PCR. Trends Genet 1995;11(6):242-246.
Schena et al., Quantitative monitoring of gene expression patterns with a complementary DNA microarray. Science 270(5235):467-470.
Shen R, Su ZZ, Olsson CA, Fisher PB. Identification of the human prostatic carcinoma oncogene PTI-1 by rapid expression cloning and differential RNA display. Proc Natl Acad Sci USA 1995;92(15):6778-6782.
Velculescu VE, Zhang L, Vogelstein B, Kinzler KW. Serial analysis of gene expression. Science 1995;270(5235):484-487.
Bett AJ, Haddara W, Prevec L, Graham FL. An efficient and flexible system for construction of adenovirus vectors with insertions or deletions in early regions 1 and 3. Proc Natl Acad Sci USA 1994;91(19):8802-8806.
Dermer, Another anniversary of the war on cancer. Bio/Technol. 1994;12:320.
Hakvoort TB, Leegwater AC, Michiels FA, Chamuleau RA, Lamers WH. Identification of enriched sequences from cDNA subtraction-hybridization procedure. Nucleic Acids Res 1994;22(5):878-879.
Hayashi Y, DePaoli AM, Burant CF, Refetoff S. Expression of a thyroid hormone-responsive recombinant gene introduced into adult mice livers by replication-defective adenovirus can be regulated by endogenous thyroid hormone receptor. J Biol Chem 1994;269(39):23872-23875.
Hubank M, Schatz Dg. Identifying differences in mRNA expression by representational difference analysis of cDNA. Nucleic Acids Res 1994;22(25):5640-5648.
Jain, Barriers to drug delivery in solid tumors. Sci. American 1994; 271:58-65.
Adams MD, Kerlavage AR, Fields C, Venter JC. 3,400 new expressed sequence tags identify diversity of transcripts in human brain. Nat Genet 1993;4(3):256-267.
Curti, Physical barriers to drug delivery in tumors. Crit. Rev. Oncol. Hematol. 1993; 14:29-39.
Jiang H, Fisher PB. A sensitive and efficient subtraction hybridization protocol for the identification of genes differentially regulated during the induction of differentiation in human melanoma cells. Mol Cell Different 1(3):285-299.
Levine, The tumor suppressor genes, Annu. Rev. Biochem. 62:623-651.
Li Q, Kay MA, Finegold M, Stratford-Perricaudet LD, Woo SL. Assessment of recombinant adenoviral vectors for hepatic gene therapy. Hum Gene Ther 1993;4(4):403-409.
Mastrangeli A, Daniel C, Rosenfeld MA, Stratford-Perricaudet L, Perricaudet M, Pavirani A, Lecocq JP, Crystal RG. Diversity of airway epithelial cell targets for in vivo recombinant adenovirus-mediated gene transfer. J Clin Invest 1993;91(1):225-234.
Ragot T, Vincent N, Chafey P, Vigne E, Gilgenkrantz H, Couton D, Cartaud J, Briand P, Kaplan JC, Perricaudet M, et al. Efficient adenovirus-mediated transfer of a human minidystrophin gene to skeletal muscle of mdx mice. Nature 1993;361(6413):647-650.
Ralph D, McClelland M, Welsh J. RNA fingerprinting using arbitrarily printed PCR identifies differentially regulated RNAs in mink lung (Mv1Lu) cells growth arrested by transforming growth factor beta 1. Proc Natl Acad Sci USA 1993;90(22):10810-10714.
Reddy PG, Su ZZ, Fisher PB. Identification and cloning of genes involved in progression of transformed phenotype. In: Chromosome and Genetic Analysis. Methods in Molecular Genetics. Adolph KW, ed. vol. I. Academic Press. 1993. pp. 68-102.
Watson JB, Margulies JE. Differential cDNA screening strategies to identify novel stage-specific proteins in the developing mammalian brain. Dev Neurosci 1993;15(2):77-86.
Jaffe HA, Danel C, Longenecker G, Metzger M, Setoguchi Y, Rosenfeld MA, Gant TW, Thorgeirsson SS, Stratford-Perricaudet LD, Perricaudet M, et al. Adenovirus-mediated in vivo gene transfer and expression in normal rat liver. Nat Genet 1992;1(5):372-378.
Liang P, Pardee AB. Differential display of eukaryotic messenger RNA by means of the polymerase chain reaction. Science 1992;257(5072):967-71.
Quantin B, Perricaudet LD, Tajbakhsh S, Mandel JL. Adenovirus as an expression vector in muscle cells in vivo. Proc Natl Acad Sci USA 1992;89(7):2581-2584.
Rangnekar VV, Waheed S, Rangnekar VM. Interleukin-1 inducible tumor growth arrest is characterized by activation of cell type-specific "early" gene expression programs. J Biol Chem 1992;267(9):6240-6248.
Rosenfeld MA, Yoshimura K, Trapnell BC, Yoneyama K, Rosenthal ER, Dalemans W, Fukayama M, Bargon J, Stier LE, Stratford-Perricaudet L, et al. In vivo transfer of the human cystic fibrosis transmembrane conductance regulator gene to the airway epithelium. Cell 1992;68(1):143-155.
Sutter G, Moss B. Nonreplicating vaccinia vector efficiently expresses recombinant genes. Proc Natl Acad Sci USA 1992;89(22):10847-10851.
Walsh CE, Liu JM, Xiao X, Young NS, Nienhuis AW, Samulski RJ. Regulated high level expression of a human gamma-globin gene introduced into erythroid cells by an adeno-associated virus vector. Proc Natl Acad Sci USA 1992;89(15):7257-7261.
Rosenfeld MA, Siegfried W, Yoshimura K, Yoneyama K, Fukayama M, Stier LE, Paakko PK, Gilardi P, Stratford-Perricaudet LD, Perricaudet M, et al. Adenovirus-mediated transfer of a recombinant alpha 1-antitrypsin gene to the lung epithelium in vivo. Science 1991;252(5004):431-434.
Wang Q, Konan V, Taylor MW. Expression of the APRT gene in an adenovirus vector system as a model for studying gene therapy. Adv Exp Med Biol 1991;309B:61-66.
Darnell et al., "Molecular Cell Biology," Scientific American Books, Inc. 1990, p. 296 and p. 344.

Duigou GJ, Babiss LE, Iman DS, Shay JW, Fisher PB. Suppression of the progression phenotype in somatic cell hybrids occurs in the absence of altered adenovirus type 5 gene expression. Mol Cell Biol 1990;10(5):2027-2034.

Fisher, ed., Model Cell Culture Systems for Studying Differentiation: Mechanisms of Differentiation. CRC Press, Boca Raton, FL, 1990;vol. 1.

Fisher, ed., Modulation of Differentiation by Exogenous Agents: Mechanisms of Differentiation. CRC Press, Boca Raton, FL, 1990;vol. 2.

Geller AI, Freese A. Infection of cultured central nervous system neurons with a defective herpes simplex virus 1 vector results in stable expression of *Escherichia coli* beta-galactosidase. Proc Natl Acad Sci USA 1990;87(3):1149-1153.

Stratford-Perricaudet LD, Levrero M, Chasse JF, Perricaudet M, Briand P. Evaluation of the transfer and expression in mice of an enzyme-encoding gene using a human adenovirus vector. Human Gene Ther 1990;1:241-256.

Voet and Voet, "Biochemistry," John Wiley & Sons, N.Y. 1990, p. 866.

Ausubel et al. Current Protocols in Molecular Biology. Green Publishing Associates, Inc. and John Wiley & Sons, Inc., New York 1989;1:2.10.3.

Duigou GJ, Babiss LE, Fisher PB. Suppression of the progression phenotype by 5-azacytidine in rat embryo cells doubly transformed by type 5 adenovirus and the Ha-*ras* oncogene. Annals NY Acad Sci 1989;567:302-306.

Huse WD, Sastry L, Iverson SA, Kang AS, Alting-Mees M, Burton DR Benkovic SJ, Lerner RA. Generation o a large combinatorial library of the immunoglobulin repertoire in phage lambda. Science 1989;246(4935):1275-1281.

Miller AD, Rosman GJ. Improved retroviral vectors for gene transfer and expression. Biotechniques 1989;7(9):980-982, 984-986, 989-990.

Hambor JE, Hauer CA, Shu HK, Groger RK, Kaplan DR, Tykocinski ML. Use of an Epstein-Barr virus episomal replicon for anti-sense RNA-mediated gene inhibition in a human cytotoxic T-cell clone. Proc Natl Acad Sci USA 1988;85(11):4010-4014.

Babiss LE, Zimmer SG, Fisher PB. Reversibility of progression of the transformed phenotype in Ad5-transformed rat embryo cells. Science 1985;228(4703):1099-101.

Cole SPC, Kozbor D, Roder JC. The EBV-hybridoma technique and its application to human lung cancer. In: Monoclonal Antibodies and Cancer Therapy. Alan R. Liss, Inc., 1985; pp. 77-96.

Takeda S, Naito T, Hama K, Noma T, Honjo T. Construction of chimaeric processed immunoglobulin genes containing mouse variable and human constant region sequences. Nature 1985;314(6010):452-454.

Morrison SL, Johnson MJ, Herzenberg LA, Oi VT. Chimeric human antibody molecules: mouse antigen-binding domains with human constant region domains. Proc Natl Acad Sci USA 1984;81(21):6851-6855.

Neuberger MS, Williams GT, Fox RO. Recombinant antibodies possessing novel effector functions. Nature 1984;312(5995):604-608.

Cote RJ, Morrissey DM, Houghton AN, Beattie EJ Jr, Oettgen HF, Old LJ. Generation of human monoclonal antibodies reactive with cellular antigens. Proc Natl Acad Sci USA 1983;80(7):2026-2030.

Freshney, Culture of animal cells, a manual of basic technique, Alan R. Liss, N.Y. 1983., p. 3-4.

Kozbor D, Roder JC. The production of monoclonal antibodies from human lymphocytes. Immunology Today 1983;4:72-79.

Fisher PB, Babiss LE, Weinstein IB, Ginsberg HS. Analysis of type 5 adenovirus transformation with a cloned rat embryo cell line (CREF). Proc Natl Acad Sci USA 1982;79(11):3527-3531.

Fisher PB, Bozzone JH, Weinstein IB. Tumor promoters and epidermal growth factor stimulate anchorage-independent growth of adenovirus-transformed rat embryo cells. Cell 1979;18(3):695-705.

Fisher PB, Dorsch-Hasler K, Weinstein IB, Ginsberg HS. Tumour promoters enhance anchorage-independent growth of adenovirus-transformed cells without altering the integration pattern of viral sequences. Nature 1979;281(5732):591-594.

Fisher PB, Goldstein NI, Weinstein IB. Phenotypic properties and tumor promoter-induced alterations in rat embryo cells transformed by adenovirus. Cancer Res 1979;39(8):3051-3057.

Fisher PB, Weinstein IB, Eisenberg D, Ginsberg HS. Interactions between adenovirus, a tumor promoter, and chemical carcinogens in transformation of rat embryo cell cultures. Proc Natl Acad Sci USA 1978;75(5):2311-2314.

Kohler G, Milstein C. Continuous cultures of fused cells secreting antibody of predefined specificity. Nature 1975;256(5517):495-7.

Michael J. Wagner, Janice Sharp, and William C. Summers Nucletide sequence of the thymidine kinase gene of herpes simplex vrus type 1. Proc Natl. Acad. Sci. USA vol. 78, No. 3 pp. 1441-1445, Mar. 1981.

Tadashi Yamamoto, Benoit de Crombrugghe and Ira Pastan Identification of a Functional Promoter in the Long Terminal Repeat of Rous Sarcoma Virus. Cell vol. 22,787-797, Dec. 1980.

Susan M. Berget, Claire Moore and Philip A. Sharp Spliced segments at the 5' terminus of adenovirus 2 late ,RNA* Proc. Natl. Acad. Sct. USA vol. 74, No. 8 pp. 3171-3175, Aug. 1977.

Louise T. Chow, Richard E. Gelinas, Thomas R. Broker and Richard J. Roberts an Amazing Sequence Arrangement at the 5' Ends of Adenovirus 2 Messenger RNA, Cell vol. 12, 1-8 , Sep. 1977.

F.L. Graham and J. Smiley Characteristics of a Human Cell Line Transformed by DNA from Human Adenovirus Type 5. J. gen. Virol (1977), 36, 59-72.

Tsuyoshi Uchida, Alwin M. Pappaenheimer, Jr. and Robin Greany Diphtheria Toxin and Related Proteins. The Journal of Biological Chemistry, vol. 248, No. 11, Issue Jun. 10, pp. 3838-3844, 1973.

M. Puttaraju, Sharon F. Jamison, S. Gary Mansfield, Mariano A. Garcio-Blanco, and Looyd G. Michell. Spliceosome-mediated RNA trans-splicing as a tool for gene therapy, vol. 17, Mar. 1999.

SG Mansfield, J. Kole, M. Pattaraju, CC Yang, MA Garcia-Blanco, JA Cohn and LG Mitchell. Repair of CFTR mRNA by spliceosome-mediated RNA trans-splicing, Gene Therapy (2000) 7, 1885-1895.

Anne K. Voss, Tim Thomas and Peter Gruss. Efficiency Assessment of the Gene Trap Approach, Developmental Dynamics 212:171-180 (1998).

Joshua T. Jones, Seong-Wook Lee & Bruce A. Sullenger, Tagging ribozyme reaction sites to follow trans-splicing in mammalian cells, Nature Medicine V 2, No. 6, Jun. 1996.

S. Bhaumik, Z. Walls, M. Puttaraju, L.G. Molecular imaging of gene expression in living subjects by spliceosome-mediated RNA trans-splicing, Jun. 8, 2004, V. 101, No. 23.

M. Puttaraju, Sharon F. Jamison, S. Gary Mansfielf, Mariano A. Garcia-Blanco, and Lloyd G. Mitchell, Spliceosome-mediated RNA trans-splicing as a tool for gene therapy, vol. 17, Mar. 1999.

M. Puttaraju, Janet DiPasquale, Carl C. Baker, Lloyd G. Mitchell, and Mariano A. Garcia-Blanco, Messenger RNA Repair and Restoration of Protein Function by Spliceosome-Mediated RNATrans-Splicing, vol. 4, No. 2, Aug. 2001.

Mariano A. Garcia-Blanco, M. Puttaraju S. Gary Mansfield and Lloyd Mitchell, Sliceosome-mediated RNA trans-splicing in gene theray and genomics, vol. 1, No. 2, pp. 141-163 (2000).

U.S. Appl. No. 10/693,192, filed Oct. 23, 2003, "Screening Method for Identification of Efficient Pre-Trans-Splicing Molecules," Mitchell et al.

U.S. Appl. No. 10/434,727, filed May 8, 2003, "Use of Sliceosome Mediated RNA Trans-Splicing to Confer Cell Selective Replication to Adenoviruses," Otto et al.

U.S. Appl. No. 10/374,784, filed Feb. 25, 2003, "Trans-Splicing Mediated Imaging of Gene Expression," Mitchell et al.

U.S. Appl. No. 10/360,787, filed Jun. 5, 2002, "Spliceosome Mediated RNA Trans-Splicing for Correction of Factor VIII Genetic Defects," Mitchell et al.

U.S. Appl. No. 10/198,447, filed Jul. 17, 2002, "Spliceosome Mediated RNA Trans-Splicing for Correction of Skin Disorders," Mitchell et al.

U.S. Appl. No. 10/136,723, filed Apr. 30, 2002, "Transgenic Animal Model for Spliceosome-mediated RNA Trans-Splicing," Puttaraju et al.

U.S. Appl. No. 10/103,294, filed Mar. 20, 2002, "Spliceosome Mediated RNA Trans-Splicing," Mitchell et al.

U.S. Appl. No. 10/075,028, filed Feb. 12, 2002, "Methods and Compositions for Use in Spliceosome Mediated RNA Trans-Splicing," Mitchell et al.

U.S. Appl. No. 10/076,248, filed Feb. 12, 2002, "Methods and Compositions for Use in Spliceosome Mediated RNA Trans-Splicing," Mitchell et al.

U.S. Appl. No. 09/838,858, filed Apr. 20, 2001, "Methods and Compositions for Use in Spliceosome Mediated RNA Trans-Splicing," Mansfield et al.

U.S. Appl. No. 09/756,097, filed Jan. 8, 2001, "Methods and Compositions for Use in Spliceosome Mediated RNA Trans-Splicing," Mitchell et al.

U.S. Appl. No. 09/756,095, filed Jan. 8, 2001, "Methods and Compositions for Use in Spliceosome Mediated RNA Trans-Splicing," Mitchell et al.

U.S. Appl. No. 09/756,096, filed Jan. 8, 2001, "Methods and Compositions for Use in Spliceosome Mediated RNA Trans-Splicing," Mitchell et al.

Bhaumik et al., "Molecular Imaging of Gene Expression in Living Subjects by Splicesome-Mediated RNA Trans-Splicing," Jun. 8, 2004, Proc. Natl. Acad. Sci., 101:23:8693-8698.

Tahara et al., "Trans-Splicing Repair of CD40-Ligand Deficiency Results in Naturally Regulated Correction of a Mouse Model of Hyper-IgM X-Linked Immunodeficiency," Aug. 2004, Nature Medicine, 10:835-841.

Chao et al., "Phenotype Correction of Hemophilia A Mice by Spliceosome-Mediated RNA Trans-Splicing," Aug. 2003, Nature Medicine, 9:1-5.

Liu et al., "Partial Correction of Endogenous Δ508 CFTR in Human Cystic Fibrosis Airway Epithelia by Spliceosome-Mediated RNA Trans-Splicing," Jan. 2002, Nature Biotechnology, 20:47-52.

Kim et al., "Role of the Nonsense-Mediated Decay Factor hUpf3 in the Splicing Dependent Exon-Exon Junction Complex," Sep. 7, 2001, Science 293:1832-1836.

Kim et al., "Replication-Selective Virotherapy for Cancer:Biological Principles, Risk Management and Future Directions," Jul. 2001, Nat. Med. 7:781-787.

Tian et al., "Strong RNA Splicing Enhancers Identified by a Modified Method of Cycled Selection Interact with SR Protein," Sep. 7, 2001, J. Biological Chemistry 276:33833-33839.

Mansfield et al., "Repair of CFTR mRNA by Splicesome-Mediated RNA Trans-Splicing," Jul. 28, 2000, Gene Therapy 7:1885-1895.

Tacke et al., "Determinants of SR Protein Specificity," 1999, Curr. Opin. Cell Biol. 11:358-362.

He et al. "A Simplified System for Generating Recombinant Adenoviruses," Mar. 1998, Proc. Natl. Acad. Sci., 95, 2509-2514.

Lan et al., "Ribozyme-Mediated Repair of Sickle β-Globin mRNAs in Erythrocyte Precursors" Jun. 5, 1998, Science 280:1593-1596.

Phylactou et al., "Ribozyme-Mediated Trans-Splicing of a Trinucleotide Repeat" Apr. 1998, Nature Genetics 18:378-381.

Staley et al., "Mechanical Devices of the Spliceosome: Motors, Clocks, Springs and Things," 1998, Cell 92:315-326.

Bellet et al., "Malignant Transformation of Nontrophoblastic Cells is Associated With the Expression of Chorionic Gonadotropin β Genes Normally Transcribed Introphoblastic Cells," Feb. 1, 1997, Cancer Res. 57:516-523.

Coolidge et al., "Functional Analysis of the Polypyrimidine Tract in Pre-mRNA Splicing," 1997, Nucleic Acids Res. 25:888-896.

Crouzet et al. "Recombinational Construction in *Escherichia coli* of Infectious Adenoviral Genomes," Feb. 1997, Proc. Natl. Acad. Sci., 94, 1414-1419.

Good et al., "Expression of Small, Therapeutic RNAs in Human Cell Nuclei," 1997, Gene Ther. 4:45-54.

Malek et al., "Evolution of Trans-Splicing Plant Mitochondrial Introns in Pre-Permian Times," Jan. 1997, Proc. Nat'l. Acad. Sci., 94:553-558.

Chartier, et al., "Efficient Generation of Recombinant Adenovirus Vectors by Homologous Recombination in *Escherichia coli*," Jul. 1996, Virol. 70, 4805-4810.

Hoon et al., "Detection of Metastatic Breast Cancer by β-hCG Polymerase Chain Reaction," 1996, Int J. Cancer 69:369-374.

Jone et al., "Tagging Ribozyme Reaction Sites to Follow Trans-Splicing in Mammalian Cells," Jun. 1996, Nature Medicine 2:643-648.

Krämer A., "The Structure and Function of Proteins Involved in Mammalian Pre-mRNA Splicing," 1996, Annu. Rev. Biochem. 65:367-409.

Miyake et al. "Efficient Generation of Recombinant Adenoviruses Using Adenovirus DNA-Terminal Protein Complex and a Cosmid Bearing the Full-Length Virus Genome," Feb. 1996, Proc. Natl. Acad. Sci., 93, 1320-1324.

Nilsson et al., "Multiple Affinity Domains for the Detection, Purification, and Immobilization of Recombinant Proteins," 1996, J. Mol. Recognition, 9:585-594.

Pasman et al., "The 5' and 3' Splice Sites Come Together Via a Three Dimensional Diffusion Mechanism," 1996, Nucleic Acids Res. 24(9):1638-1645.

Boelens et al., "Nuclear Retention of RNA as a Mechanism for Localization" 1995, RNA 1:273-283.

Bruzik et al., "Enhancer-Dependent Interaction Between 5' and 3' Splice Sites in Trans," 1995, Proc. Nat'l. Acad. Sci., 92:7056-7059.

Chiara et al., "A Two-Step Mechanism for 5' and 3' Splice-Site Pairing," Jun. 1995, Nature 375:510-513.

Davis et al., "RNA Trans-Splicing in Flatworms," Sep. 15, 1995, J. Biol. Chem. 270:21813-21819.

Eul et al., "Experimental Evidence for RNA Trans-Splicing in Mammalian Cells," 1995, EMBO. J. 14(13):3226-3235.

Xiang-Dong Fu, "The Superfamily of Arginine/Serine-Rich Splicing Factors," 1995, RNA 1:663-680.

Bett et al. "An Efficient and Flexible System for Construction of Adenovirus Vectors with Insertions or Deletions in Early Regions 1 and 3," Sep. 1994, Proc. Natl. Acad. Sci., 91,8802-8806.

Hollenberg et al., "Multiple Promoter Elements in the Human Chorionic Gonadotropin B Subunit Genes Distinguish their Expression from Luteinizing Hormone β Gene," 1994, Mol. Cell Endo., 106:111-119.

Ketner et al. "Efficient Manipulation of the Human Adenovirus Genome as an Infectious Yeast Artificial Chromosome Clone," Jun. 1994, Proc. Natl. Acad. Sci., 91, 6186-6190.

Sullenger et al., "Ribozyme-Mediated Repair of Defective mRNA by Targeted Trans-Splicing," Oct. 1994, Nature 371:619-622.

Goldspiel et al., "Human Gene Therapy," Jul. 1993, Clinical Pharmacy 12:488-505.

Kozarsky and Wilson et al., "Gene Therapy: Adenovirus Vectors," 1993, Current Opinion in Genetics and Development 3:499-503.

Miller and Rosman, "Use of Retroviral Vectors for Gene Transfer and Expression," 1993, Meth. Enzymol. 217:581-599.

Moore and Sharp, "Evidence for Two Active Sites in the Splicesome Provided by Stereochemistry of Pre-mRNA Splicing," Sep. 23, 1993, The Nature, 365:364-368.

Moore et al, "Splicing of Precursors to mRNA by The Spliceosome," 1993, RNA World, 303-357.

Morgan and Anderson, "Human Gene Therapy," 1993, Ann. Rev. Biochem. 62:191-217.

Mulligan, Richard C., "The Basic Science of Gene Therapy," May 14, 1993, Science 260:926-932.

Roscigno et al., "A Mutational Analysis of the Polypyrimidine Tract of Introns," May 25, 1993, J. Bio. Chem., 268:11222-11229.

Tolstoshev, Paul, "Gene Therapy, Concepts, Current Trials, and Future Directions," 1993, Ann. Rev. Pharmacol. Toxicol. 33:573-596.

Acevedo et al., "Human Chorionic Gonadotropin-Beta Subunit Gene Expression in Cultured Human Fetal and Cancer Cells of Different Types and Origins," Oct. 15, 1995, Cancer 76:1467-1475.

Bruzik et al., "Spliced Leader RNAs from Lower Eukaryotes are Trans-spliced in Mammalian Cells," Dec. 1992, Nature 360:692-695.

Vellard et al., "A Potential Splicing Factor is Encoded by the Opposite Strand of the Trans-Spliced C-myb Exon," 1992, Proc. Nat'l. Acad. Sci., 89:2511-2515.

Dingwall and Laskey, "Nuclear Targeting Sequences—A Consensus?" Dec. 1991, Trends in Biochem. Sci., 16:478-481.

Ghattas et al., "The Encephalomyocarditis Virus Internal Ribosome Entry Site Allows Efficient Coexpression of Two Genes from a Recombinant Provirus in Culture Cells and in Embryos," Dec. 1991, Mol. Cell Biol. 11:5848-5859.

Janknecht et al., "Rapid and Efficient Purification of Native Histidine-Tagged Protein Expressed by Recombinant Vaccinia Virus," Jul. 8, 1991, Proc. Natl. Acad. Sci., 88:8972-8976.

Rosenfeld et al. "Adenovirus-Mediated Transfer of a Recombinant $\alpha_{-1}$ Antitrypsin Gene to the Lung Epithelium in Vivo," Apr. 19, 1991, Science, 252, 431-4.

Wu and Wu, "Delivery Systems for Gene Therapy," 1991, Biotherapy 3:87-95.

Gilardi et al. "Expression of Human $\alpha_{-1}$-Anti-trypsin Using a Recombinant Adenovirus Vector," 1990, EBS Lett. 267, 60-62.

Rajkovic et al., "A Spliced Leader is Present on a Subset of mRNAs from the Human Parasite Schistosoma Mansoni" Nov. 1990, Proc. Nat'l. Acad. Sci., 87:8879-8883.

Schneider and Banes, "Building Blocks for Oligonucleotide Analogs with Dimethylene-Sulfide-Sulfoxide and Sulfone Groups Replacing Phosphodiester Linkages," 1990, Tet. Letters, 31:335-338.

Senapathy et al., "Splice Junctions, Branch Point Sites, and Exons-:Sequence Statistics, Identification, and Applications to Genome Project," 1990, Methods in Enzymology, 183:252-278.
Uhlmann and Peyman, "Antisense Oligonucleotides: A New Therapeutic Principle," Jun. 1990, Chemical Reviews, 90:543-584.
Kerem et al., "Identification of the Cystic Fibrosis Gene: Genetic Analysis," Sep. 8, 1989, Science, 245:1073-1080.
Letsinger et al., "Cholesteryl-Conjugated Oligonucleotide: Synthesis, Properties, and Activity as Inhibitors of Replication of Human Immunodeficiency Virus in Cell Culture," Sep. 1989, Proc. Natl. Acad. Sci., 86:6553-6556.
Reed, Robin, "The Organization of 3' Splice Sites Sequences in Mammalian Introns," 1989, Genes Dev. 3:2113-2123.
Riordan et al., "Identification of the Cystic Fibrosis Gene: Cloning and Characterization of Complementary DNA," 1989, Science, 245:1066-1073.
Rommens et al., "Identification of the Cystic Fibrosis Gene: Chromosome Walking and Jumping," Sep. 8, 1989, Science, 245:1059-1065.
Shimizu et al., "Immunoglobulin Double-Isotype Expression by Trans-mRNA in a Human Immunoglobulin Transgenic Mouse," Oct. 1989, Proc. Nat'l. Acad. Sci. 86:8020-8023.
Smith et al., "Scanning From an Independently Specified Branch Point Defines the 3' Splice Site of Mammalian Introns," 1989, Nature, 342:243-247.
Van der Krol et al., "Modulation of Eukaryotic Gene Expression by Complementary RNA or DNA Sequences," 1988, BioTechniques, 6:958-976.
Reed & Maniatis, "The Role of the Mammalian Branchpoint Sequence in the Pre-mRNA Splicing," 1988, Genes Dev. 2:1268.
Smith et al, "Single-Step Purification of Polypeptides Expressed in *Escherichia coli* as Fusions with Glutathione S-Transferase," 1988, Gene, 67:31.
Zon et al., "Oligonucleotide Analogues as Potential Chemotherapeutic Agents," 1988, Pharm. Res., 5:539-549.
Krause M et al., "A Trans-Spliced Leader Sequence on Actin mRNA in *C. elegans*," 1987, Cell 49:753-761.
Lemaitre et al., "Specific Antiviral Activity of a Poly(L-lysine)-Conjugated Oligodeoxyribonucleotide Sequence Complementary to Vesicular Stomatitis Virus N Protein mRNA Initiation Site," 1987, Proc. Natl. Acad. Sci., 84:648-652.
Wu and Wu, "Receptor-Mediated in Vitro Gene Transformation by a Soluble DNA Carrier System," 1987, J. Biol. Chem., 262:429-4432.
Dingwall and Laskey, "Protein Import into the Cell Nucleus," 1986, Ann. Rev. Cell Biol. 2:367-390.
Murphy et al., "Identification of a Novel Y Branch Structure as an Intermediate in Trypanosome mRNA Processing: Evidence for Trans Splicing," 1986, Cell, 47:517.
Smith et al., "Mv 26,000 Antigen of *Schistosoma japonicum* Recognized by Resistant WEH1 129/J Mice is a Parasite Glutathione S-Transferase," 1986, Proc. Natl. Acad. Sci., 83:8703-8707.
Sutton et al., "Evidence for Trans Splicing in Trypanosomes," 1986, Cell 47:527-535.
Konarska et al., "Trans Splicing of mRNA Precursors in Vitro" 1985, Cell 46:165-171.
Solnick et al, "Trans Splicing of mRNA Precursors," 1985, Cell 42:157-164.
Talmadge et al., "Only Three of the Seven Human Chorionic Gonadotropin Beta Subunit Genes can be Expressed in the Placenta," 1984, Nucleic Acids Res. 12:8415.
Accession No. K01722, Corynebacteriophage beta diptheria toxin (DT) gene, Apr. 27, 1993.
Berkner, et al. "Generation of Adenovirus by Transfection of Plasmids," 1983, Nucleic Acids Res. 11, 6003-6020.
Greenfield, "Nucleotide Sequence of the Structural Gene for the Diptheria Toxin Carried by Corynebacteriophage β," 1983, Proc. Natl. Acad. Sci., 80:6853-6857.

Brinster et al., "Regulation of Metallothionein-Thymidine Kinase Fusion Plasmids Injected into Mouse Eggs," 1982, Nature 296:39-42.
Benoist et al., "In Vivo Sequence Requirements of the SV40 Early Promoter Region," 1981, Nature, 290:304-310.
Wagner et al., "Nucleotide Sequence of the Thymidine Kinase Gene of Herpes Simplex Virus Type 1," Mar. 1981, Proc. Natl. Acad. Sci., 78(3):1441-1445.
Yamamoto et al., "Identification of a Functional Promoter in the Long Terminal Repeat of Rous Sarcoma Virus," 1980, Cell, 22:787-797.
Berget et al., Spliced Segments at the 5' Terminus of Adenovirus 2 Late mRNA, 1977, Proc. Natl. Acad. Sci., 74(8):3171-3175.
Chow et al., "An Amazing Sequence Arrangement at the 5' Ends of Adenovirus 2 Messenger RNA," 1977, Cell 12:1-8.
Graham et al., "Characteristics of a Human Cell Line Transformed by DNA from Human Adenovirus Type 5," 1977, J. Gen. Virol. 36:59-72.
Uchida et al, "Diptheria Toxin and Related Proteins: Isolation and Properties of Mutant Proteins Related to Diptheria Toxin," 1973 J. Biol. Chem., 248:3838.
Puttaraju et al., Spliceosome-Mediated RNA Trans-Splicing as a Tool for Gene Therapy, Nat. Biotech., 1999, vol. 17, 246-252.
Voss et al., "Efficiency Assessment of the Gene Trap Approach", 1998, Development Dynamics, 212:171-180.
Puttaraju et al., "Messenger RNA Repair and Restoration of Protein Function by Spliceosome-Mediated mRNA Trans-Splicing", Mol. Therapy, 2001, vol. 4, 105-114.
Song et al., "Intramuscular Administration of Recombinant Adeno-Associated Virus 2 X-1 Antitrypsin (rAAV-SERPINA1) Vectors in a Nonhuman Primate Model: Safety and Immunologic Aspects", Sep. 3, 2002, Molecular Therapy 6:329-335.
Garcia-Blanco et al, "Spliceosome-Mediated RNA Trans-Splicing in Gene Therapy and Genomics," Apr. 20, 2000, Gene Therapy and Regulation, 1:141-163.
Garcia-Blanco et al "Mending the Message", Nat. Biotech., 2003, vol. 21, No. 12, 1448-1449.
Liu et al., "Spliceosome-Mediated RNA Trans-Splicing with Recombinant Adeno-Associated Virus Partially Restores Cystic Fibrosis Transmembrane Conductance Regulator Function to Polarized Human Cystic Fibrosis Airway Epithelial Cells," Sep. 2005 *Human Gene Therapy* 16:1116-1123.
Mansfield, et al. "5' Exon Replacement and Repair by Spliceosome-Mediated RNA Trans-Splicing", RNA, 2003, vol. 9, 1290-1297.
Mansfield et al., Repair of CFTR mRNA by Spliceosome-Mediated RNA Trans-Splicing, Gene Therapy, 2000, vol. 7, 1885-1895.
Manzano, et al., "Failure to Generate Atheroprotective Apolipoprotein Al Phenotypes Using Synthetic RNA/DNA Oligonucleotides (chimeraplasts)", J. Gene Med., 2003, vol. 5, 795-802.
Parolini, et al., "Targeted Replacement of Mouse Apolipoprotein A-I with Human ApoA-I or the Mutant ApoA-I", J. Bio. Chem., 2003, vol. 278, 4740-4746.
Martinez-Sales, E., Internal Ribosome Entry Site Biology and Its Use in Expression Vectors, 1999, Current Opinion in Biology, 10:458-464.
Kikumori et al., "Promiscuity of Pre-mRNA Spliceosome-Meidated Trans Splicing: A Problem for Gene Therapy?," Jul. 20, 2001, Human Gene Therapy, 12:1429-1441.
U.S. Appl. No. 09/941,492, filed Aug. 29, 2001, "Methods and Compositions for Use in Spliceosome Mediated RNA Trans-Splicing," Mitchell et al.
U.S. Appl. No. 08/786,531, filed Jan. 21, 1997, "Vehicles for Stable Transfer of Green Fluorescent Protein Gene and Methods of Use for Same," Link. Jr., et al.

* cited by examiner

Figure 2. Phenotypes of Inherited PI Deficiency

SEQUENCE LISTING

<160> NUMBER OF SEQ ID NOS: 15

<210> SEQ ID NO 1
<211> LENGTH: 6
<212> TYPE: DNA
<213> ORGANISM: Artificial
<220> FEATURE:
<223> OTHER INFORMATION: Chemically Synthesized

<400> SEQUENCE: 1 gctagc                                                                     6

<210> SEQ ID NO 2
<211> LENGTH: 6
<212> TYPE: DNA
<213> ORGANISM: Artificial
<220> FEATURE:
<223> OTHER INFORMATION: Chemically Synthesized

<400> SEQUENCE: 2 ccgcgg                                                                     6

<210> SEQ ID NO 3
<211> LENGTH: 39
<212> TYPE: DNA
<213> ORGANISM: Artificial

```
<220> FEATURE:
<223> OTHER INFORMATION: Chemically Synthesized

<400> SEQUENCE: 3
tactaactca attttttttt tttttttttt aattaacag                           39

<210> SEQ ID NO 4
<211> LENGTH: 8
<212> TYPE: RNA
<213> ORGANISM: Artificial
<220> FEATURE:
<223> OTHER INFORMATION: Chemically Synthesized

<400> SEQUENCE: 4 agguragu                                                             8

<210> SEQ ID NO 5
<211> LENGTH: 7
<212> TYPE: RNA
<213> ORGANISM: Artificial
<220> FEATURE:
<223> OTHER INFORMATION: Chemically Synthesized
<220> FEATURE:
<221> NAME/KEY: misc_feature
<222> LOCATION: (2)..(2)
<223> OTHER INFORMATION: n is a, c, g, or u

<400> SEQUENCE: 5 ynyurac                                                              7

<210> SEQ ID NO 6
<211> LENGTH: 258
<212> TYPE: DNA
<213> ORGANISM: Artificial
<220> FEATURE:
<223> OTHER INFORMATION: Chemically Synthesized

<400> SEQUENCE: 6
gtagttcttt tgttcttcac tattaagaac ttaatttggt gtccatgtct cttttttttt    60
ctagtttgta gtgctggaag gtattttkgg agaaattctt acatgagcat taggagaatg   120
tatgggtgta gtgtcttgta taatagaaat tgttccactg ataatttact ctagtttttt   180
atttcctcat attattttca gtggcttttt cttccacatc tttatatttt gcaccacatt   240
caacactgta gcggccgc                                                 258

<210> SEQ ID NO 7
<211> LENGTH: 270
<212> TYPE: DNA
<213> ORGANISM: Artificial
<220> FEATURE:
<223> OTHER INFORMATION: Chemically Synthesized

<400> SEQUENCE: 7
ccaactatct gaatcatgtg ccccttctct gtgaacctct atcataatac ttgtcacact    60
gtattgtaat tgtctctttt actttcccct gtatcttttg tgcatagcag agtacctgaa   120
acaggaagta ttttaaatat tttgaatcaa atgagttaat agaatcttta caaataagaa   180
tatacacttc tgcttaggat gataattgga ggcaagtgaa tcctgagcgt gatttgataa   240
tgacctaata atgatgggtt ttatttccag                                    270

<210> SEQ ID NO 8
<211> LENGTH: 23
<212> TYPE: DNA
<213> ORGANISM: Artificial
```

```
<220> FEATURE:
<223> OTHER INFORMATION: Chemically Synthesized

<400> SEQUENCE: 8
taatacgact cactataggg aga                                              23

<210> SEQ ID NO 9
<211> LENGTH: 23
<212> TYPE: DNA
<213> ORGANISM: Artificial
<220> FEATURE:
<223> OTHER INFORMATION: Chemically Synthesized
<220> FEATURE:
<221> NAME/KEY: misc_feature
<222> LOCATION: (22)..(22)
<223> OTHER INFORMATION: n is a, c, g, or t

<400> SEQUENCE: 9
atttaggtga cactatagaa gng                                              23

<210> SEQ ID NO 10
<211> LENGTH: 23
<212> TYPE: DNA
<213> ORGANISM: Artificial
<220> FEATURE:
<223> OTHER INFORMATION: Chemically Synthesized

<400> SEQUENCE: 10
aattaaccct cactaaaggg aga                                              23

<210> SEQ ID NO 11
<211> LENGTH: 187
<212> TYPE: DNA
<213> ORGANISM: Artificial
<220> FEATURE:
<223> OTHER INFORMATION: Chemically Synthesized

<400> SEQUENCE: 11
tattctacat atacagtata cacaaggaca ttaaaggctc tgaaaagttc tgcagagctg      60
tcagtagttt tgacagttta atctattatt tcctcaaatt actcaatgat ggaaaacatt    120
ttagtgtttg tgtgtagaaa actgaagaat ccacgctgaa aagcattgct atggcccata    180
atgcatt                                                              187

<210> SEQ ID NO 12
<211> LENGTH: 227
<212> TYPE: DNA
<213> ORGANISM: Artificial
<220> FEATURE:
<223> OTHER INFORMATION: Chemically Synthesized

<400> SEQUENCE: 12
aatgcattgt ttttgtcaaa agctaattgt gttagaggca ggatttgaac ccaggtcttt      60
cagattgcaa aactgatact gatttttgtt ctatagttct aagcattata tattctacat    120
atacagtata cacaaggaca ttaaaggctc tgaaaagttc tgcagagctg tcagtagttt    180
tgacagttta atctattatt tcctcaaatt actcaatgat ggaaaac                  227

<210> SEQ ID NO 13
<211> LENGTH: 168
<212> TYPE: DNA
<213> ORGANISM: Artificial
<220> FEATURE:
<223> OTHER INFORMATION: Chemically Synthesized

<400> SEQUENCE: 13
```

```
ttccatgaaa ctatcccttt atgcagtgta ttacaatttg ttctatagtt ctaagcatta      60
tatattctac atatacagta tacacaagga cattaaaggc tctgaaaagt tctgcagagc     120
tgtcagtagt tttgacagtt taatctatta tttcctcaaa ttactcaa                 168

<210> SEQ ID NO 14
<211> LENGTH: 297
<212> TYPE: DNA
<213> ORGANISM: Artificial
<220> FEATURE:
<223> OTHER INFORMATION: Chemically Synthesized

<400> SEQUENCE: 14 tcccagctttt ctcattggac agaaggagga gactggggct ggagagggac ctgggccccc     60
actaaggcca cagcagagcc aggactttag ctgtgctgac tgcagcctgg ctgctctcca    120
ctgccctgta gaatgcattg tttttgtcaa aagctaattg tgttagaggc aggatttgaa    180
cccaggtctt tcagattgca aaactgatac tgattctggg acactagagt cgtgtaaagt    240
atgctccatg aaactatccc tttatgcagt gtattacaat ttgttctata gttctaa       297

<210> SEQ ID NO 15
<211> LENGTH: 94
<212> TYPE: DNA
<213> ORGANISM: Artificial
<220> FEATURE:
<223> OTHER INFORMATION: Chemically Synthesized

<400> SEQUENCE: 15
ctatgctgtt ttcctgggac agtgggagct ggcttagaat gccctggggc ccccaggacc     60
ctagcatttt aaccctcag gggcaggaag gcag                                  94
```

US 8,053,232 B2

CORRECTION OF ALPHA-1-ANTITRYPSIN GENETIC DEFECTS USING SPLICEOSOME MEDIATED RNA TRANS SPLICING

CROSS-REFERENCE TO RELATED APPLICATIONS

The present application claims benefit to provisional application No. 60/538,797 filed on Jan. 23, 2004.

1. INTRODUCTION

The present invention provides methods and compositions for generating novel nucleic acid proteins through targeted spliceosome mediated RNA trans-splicing. The compositions of the invention include pre-trans-splicing molecules (PTMs) designed to interact with a SERPINA1 target precursor messenger RNA molecule (target pre-mRNA) and mediate a trans-splicing reaction resulting in the generation of a novel chimeric RNA molecule (chimeric RNA). The methods and compositions of the invention can be used in cellular gene repair for the treatment of alpha-1-antitrypsin (AAT) deficiencies and associated lung and liver pathologies.

In particular, the PTMs of the present invention include those genetically engineered to interact with SERPINA1 target pre-mRNA so as to result in correction of SERPINA1 genetic defects responsible for AAT deficiency. The PTMs of the invention may also comprise sequences that are processed out of the PTM to yield duplex siRNA, ribozymes, and/or antisense molecules directed specifically to mutant SERPINA1 mRNAs. Such duplexed siRNAs, ribozymes, and/or antisense molecules are designed to reduce the accumulation of toxic AAT protein in liver cells. The siRNAs, ribozymes, and/or antisense molecules may be encoded within an intron of the PTM or within the trans-splicing domain of the PTM. The siRNA, ribozymes, and/or antisense are designed to bind specifically to mutant SERPINA1 transcripts and not to the SERPINA1 sequences (encoding the normal protein) in the PTM because isocodon substitutions are incorporated into the PTM exons that are to be used to replace defective SERPIN A1 mRNA. The number and position of the isocodon substitutions used are sufficient to prevent the siRNA, ribozyme, and/or antisense sequences from binding to or interacting with the PTM encoded SERPINA1 sequences.

The compositions of the invention further include recombinant vector systems capable of expressing the PTMs of the invention and cells expressing said PTMs. The methods of the invention encompass contacting the PTMs of the invention with a SERPINA1 target pre-mRNA under conditions in which a portion of the PTM is trans-spliced to a portion of the target pre-mRNA to form a mRNA molecule wherein the genetic defect in the SERPINA1 gene has been corrected and/or where SERPINA1 siRNA molecules are expressed, reducing the accumulation of toxic AAT protein in liver cells. The methods and compositions of the present invention can be used in gene therapy for correction of SERPINA1 disorders such as AAT deficiency.

2. BACKGROUND OF THE INVENTION

2.1 RNA Splicing

DNA sequences in the chromosome are transcribed into pre-mRNAs which contain coding regions (exons) and generally also contain intervening non-coding regions (introns). Introns are removed from pre-mRNAs in a precise process called cis-splicing (Chow et al., 1977, *Cell* 12:1-8; and Berget, S. M. et al., 1977, *Proc. Natl. Acad. Sci. USA* 74:3171-3175). Splicing takes place as a coordinated interaction of several small nuclear ribonucleoprotein particles (snRNP's) and many protein factors that assemble to form an enzymatic complex known as the spliceosome (Moore et al., 1993, in The RNA World, R. F. Gestland and J. F. Atkins eds. (Cold Spring Harbor Laboratory Press, Cold Spring Harbor, N.Y.); Kramer, 1996, *Annu. Rev. Biochem.*, 65:367-404; Staley and Guthrie, 1998, *Cell* 92:315-326).

In most cases, the splicing reaction occurs within the same pre-mRNA molecule, which is termed cis-splicing. Splicing between two independently transcribed pre-mRNAs is termed trans-splicing. Trans-splicing was first discovered in trypanosomes (Sutton & Boothroyd, 1986, *Cell* 47:527; Murphy et al., 1986, *Cell* 47:517) and subsequently in nematodes (Krause & Hirsh, 1987, *Cell* 49:753); flatworms (Rajkovic et al., 1990, *Proc. Nat'l. Acad. Sci. USA*, 87:8879; Davis et al., 1995, *J. Biol. Chem.* 270:21813) and in plant mitochondria (Malek et al., 1997, *Proc. Nat'l. Acad. Sci. USA* 94:553). In the parasite *Trypanosoma brucei*, all mRNAs acquire a splice leader (SL) RNA at their 5' termini by trans-splicing. A 5' leader sequence is also trans-spliced onto some genes in *Caenorhabditis elegans*. This mechanism is appropriate for adding a single common sequence to many different transcripts.

The mechanism of splice leader trans-splicing, which is nearly identical to that of conventional cis-splicing, proceeds via two phosphoryl transfer reactions. The first causes the formation of a 2'-5' phosphodiester bond producing a 'Y' shaped branched intermediate, equivalent to the lariat intermediate in cis-splicing. The second reaction, exon ligation, proceeds as in conventional cis-splicing. In addition, sequences at the 3' splice site and some of the snRNPs which catalyze the trans-splicing reaction, closely resemble their counterparts involved in cis-splicing.

Trans-splicing may also refer to a different process, where an intron of one pre-mRNA interacts with an intron of a second pre-mRNA, enhancing the recombination of splice sites between two conventional pre-mRNAs. This type of trans-splicing was postulated to account for transcripts encoding a human immunoglobulin variable region sequence linked to the endogenous constant region in a transgenic mouse (Shimizu et al., 1989, *Proc. Nat'l. Acad. Sci. USA* 86:8020). In addition, trans-splicing of c-myb pre-RNA has been demonstrated (Vellard, M. et al. *Proc. Nat'l. Acad. Sci.*, 1992 89:2511-2515) and more recently, RNA transcripts from cloned SV40 trans-spliced to each other were detected in cultured cells and nuclear extracts (Eul et al., 1995, *EMBO. J.* 14:3226). However, naturally occurring trans-splicing of mammalian pre-mRNAs is thought to be a rare event (Flouriot G. et al., 2002 *J. Biol. Chem*: Finta, C. et al., 2002 *J. Biol Chem* 277:5882-5890).

In vitro trans-splicing has been used as a model system to examine the mechanism of splicing by several groups (Konarska & Sharp, 1985, *Cell* 46:165-171 Solnick, 1985, *Cell* 42:157; Chiara & Reed, 1995, *Nature* 375:510; Pasman and Garcia-Blanco, 1996, *Nucleic Acids Res.* 24:1638). Reasonably efficient trans-splicing (30% of cis-spliced analog) was achieved between RNAs capable of base pairing to each other, whereas splicing of RNAs not tethered by base pairing was further diminished by a factor of 10. Other in vitro trans-splicing reactions not requiring obvious RNA-RNA interactions among the substrates were observed by Chiara & Reed (1995, *Nature* 375:510), Bruzik J. P. & Maniatis, T. (1992, *Nature* 360:692) and Bruzik J. P. and Maniatis, T., (1995, *Proc. Nat'l. Acad. Sci. USA* 92:7056-7059). These reactions occur at relatively low frequencies and require specialized elements, such as a downstream 5' splice site or exonic splicing enhancers.

In addition to splicing mechanisms involving the binding of multiple proteins to the precursor mRNA which then act to correctly cut and join RNA, a third mechanism involves cutting and joining of the RNA by the intron itself, by what are termed catalytic RNA molecules or ribozymes. The cleavage activity of ribozymes has been targeted to specific RNAs by engineering a discrete "hybridization" region into the ribozyme. Upon hybridization to the target RNA, the catalytic region of the ribozyme cleaves the target. It has been suggested that such ribozyme activity would be useful for the inactivation or cleavage of target RNA in vivo, such as for the treatment of human diseases characterized by production of foreign of aberrant RNA. In such instances small RNA molecules are designed to hybridize to the target RNA and by binding to the target RNA prevent translation of the target RNA or cause destruction of the RNA through activation of nucleases. The use of antisense RNA has also been proposed as an alternative mechanism for targeting and destruction of specific RNAs.

Using the *Tetrahymena* group I ribozyme, targeted trans-splicing was demonstrated in *E. coli*. (Sullenger B. A. and Cech. T. R., 1994, *Nature* 341:619-622), in mouse fibroblasts (Jones, J. T. et al., 1996, *Nature Medicine* 2:643-648), human fibroblasts (Phylacton, L. A. et al. *Nature Genetics* 18:378-381) and human erythroid precursors (Lan et al., 1998, *Science* 280:1593-1596). For a review of clinically relevant technologies to modify RNA see Sullenger and Gilboa, 2002 *Nature* 418:252-8. The present invention relates to the use of targeted trans-splicing mediated by native mammalian splicing machinery, i.e., spliceosomes, to reprogram or alter the coding sequence of a targeted m-RNA.

U.S. Pat. Nos. 6,083,702, 6,013,487 and 6,280,978 describe the use of PTMs to mediate a trans-splicing reaction by contacting a target precursor mRNA to generate novel chimeric RNAs.

2.2 Alpha-1-Antitrypsin Deficiency

Alpha-1-antitrypsin (AAT) is a 52 kd glycoprotein that binds to and inactivates neutrophil elastase, PR-3, and various other proteases (For comprehensive reviews, see: ATS/ERS Statement. 2003. Am J Respir Crit Care Med 168:818-900; NCBI OMIM 107400). AAT is one member of a family of serine protease inhibitors, collectively known as serpins. Deficiency of AAT is one of the most common serious genetic disorders of humans (Crystal, R. Trends Genet. 5:411-7; de Serres, F J. 2002. Chest 122:1818-1829). The most severe form (PI-ZZ) of alpha1 anti-trypsin (AAT) deficiency occurs in patients who are homozygous for a single base change (GAG→AAG) in exon 5 of the human SERPINA1 gene on human chromosome 14q32.1. The defective AAT protein accumulates in the liver, its primary site of synthesis, failing to reach the bloodstream at levels that normally protect the lung against proteolytic attack by neutrophil elastase and other resident proteases (Carrell, R W and Lomas, D A. 2003. N Engl J. Med. 346: 45-53; Primhak, R A and Tanner, M S. 2001. Arch Dis Child. 85: 2-5). Moreover, the PI-Z form of AAT protein that does reach the circulation is less potent than the normal AAT protein at neutralizing proteases. As a result, over half the PI-ZZ patients develop significant pulmonary emphysema, which commonly progresses to become life-threatening; about 30% of those who survive their lung disease to age 50 or more develop hepatic cirrhosis and hepatocellular carcinoma. The observed correlation between blood AAT levels and severity of lung disease suggests that therapeutic interventions which raise serum levels of AAT above 11 uM should protect patients against the lung disease of AAT deficiency. In fact, modest clinical improvements have been observed in patients supplemented with weekly injections of purified AAT protein that sustain this level, mainly in those with moderate airway obstruction. However, the effectiveness of this therapy is still suboptimal. In contrast, for PI-ZZ liver disease no therapy, short of liver transplantation, currently exists (ATS/ERS Statement. 2003. Am J Respir Crit Care Med 168:818-900).

The present invention provides methods and compositions for correcting defects in the SERPINA1 gene using spliceosome mediated trans-splicing. The use of trans-splicing provides a means for targeting gene therapy to only those cells expressing the mutant SERPINA1 transcript, as well as providing through expression of siRNA a means for reducing the toxic accumulation of mutant AAT protein within liver cells.

3. SUMMARY OF THE INVENTION

The present invention relates to compositions and methods for generating novel nucleic acid molecules through spliceosome-mediated targeted RNA trans-splicing, ribozyme-mediated trans-splicing, or other means of converting pre-mRNA. The compositions of the invention include pre-trans-splicing molecules (hereinafter referred to as "PTMs") designed to interact with a SERPINA1 target pre-mRNA molecule (hereinafter referred to as "SERPINA1 pre-mRNA") and mediate a spliceosomal trans-splicing reaction resulting in the generation of a novel chimeric RNA molecule (hereinafter referred to as "chimeric RNA"). The methods of the invention encompass contacting the PTMs of the invention with a natural (normal or mutant) SERPINA1 target pre-mRNA under conditions in which a portion of the PTM is spliced to the natural SERPINA1 pre-mRNA to form a novel chimeric RNA.

The PTMs of the invention are genetically engineered so that the novel chimeric RNA resulting from the trans-splicing reaction encodes a protein that complements the defective or inactive SERPINA1 protein in the cell. Generally, the target pre-mRNA is chosen because it is expressed within a specific cell type thereby providing a means for targeting expression of the novel chimeric RNA to a selected cell type. The PTMs of the invention are designed to correct genetic mutations in the SERPINA1 gene found to be associated with genetic diseases such as AAT. Such methods and compositions can be used to reduce the lung and liver pathologies associated with AAT.

In particular, the compositions of the invention include pre-trans-splicing molecules designed to interact with a defective SERPINA1 target pre-mRNA molecule and mediate a spliceosomal trans-splicing reaction resulting in the generation of a novel chimeric RNA molecule in which the defect in the SERPINA1 RNA has been corrected. In addition, the trans-splicing reaction reduces or eliminates expression from the defective (PI-Z) target pre-mRNA participating in the reaction, thereby reducing the accumulation of toxic AAT protein in hepatocytes. Additionally, the PTMs may be designed to express, upon processing, duplex siRNA molecules designed to reduce the accumulation of toxic AAT protein in liver cells.

The methods of the invention specifically encompass contacting the PTMs of the invention with a SERPINA1 target pre-mRNA comprising a genetic defect under conditions in which a portion of the PTM is spliced to the target pre-mRNA to form a novel chimeric RNA. The methods of the invention comprise contacting the PTMs of the invention with a cell expressing a SERPINA1 target pre-mRNA under conditions in which the PTM is taken up by the cell and a portion of the synthetic PTM is trans-spliced to a portion of the target pre-mRNA to form a novel chimeric RNA molecule that results in correction of a SERPINA1 genetic defect. Alternatively, nucleic acid molecules encoding PTMs may be delivered into a target cell followed by expression of the nucleic acid molecule to form a PTM capable of mediating a trans-splicing reaction. The PTMs of the invention are genetically engineered so that the novel chimeric RNA resulting from the trans-splicing reaction encodes a protein that complements or corrects a defective or inactive SERPINA1 encoded serine protease inhibitor. The methods and compositions of the invention can be used in gene repair for the treatment of various diseases including, but not limited to, genetic disorders of SERPINA1, such as AAT deficiency.

4. BRIEF DESCRIPTION OF THE DRAWINGS

FIG. 1 shows a schematic representation of different trans-splicing reactions. (a) trans-splicing reactions between the target 5' splice site and PTM's 3' splice site, (b) trans-splicing reactions between the target 3' splice site and PTM's 5' splice site and (c) replacement of an internal exon by a double trans-splicing reaction in which the PTM carries both 3' and 5' splice sites. BD, binding domain; BP, branch point sequence; PPT, polypyrimidine tract; and ss, splice sites.

Figure 1:
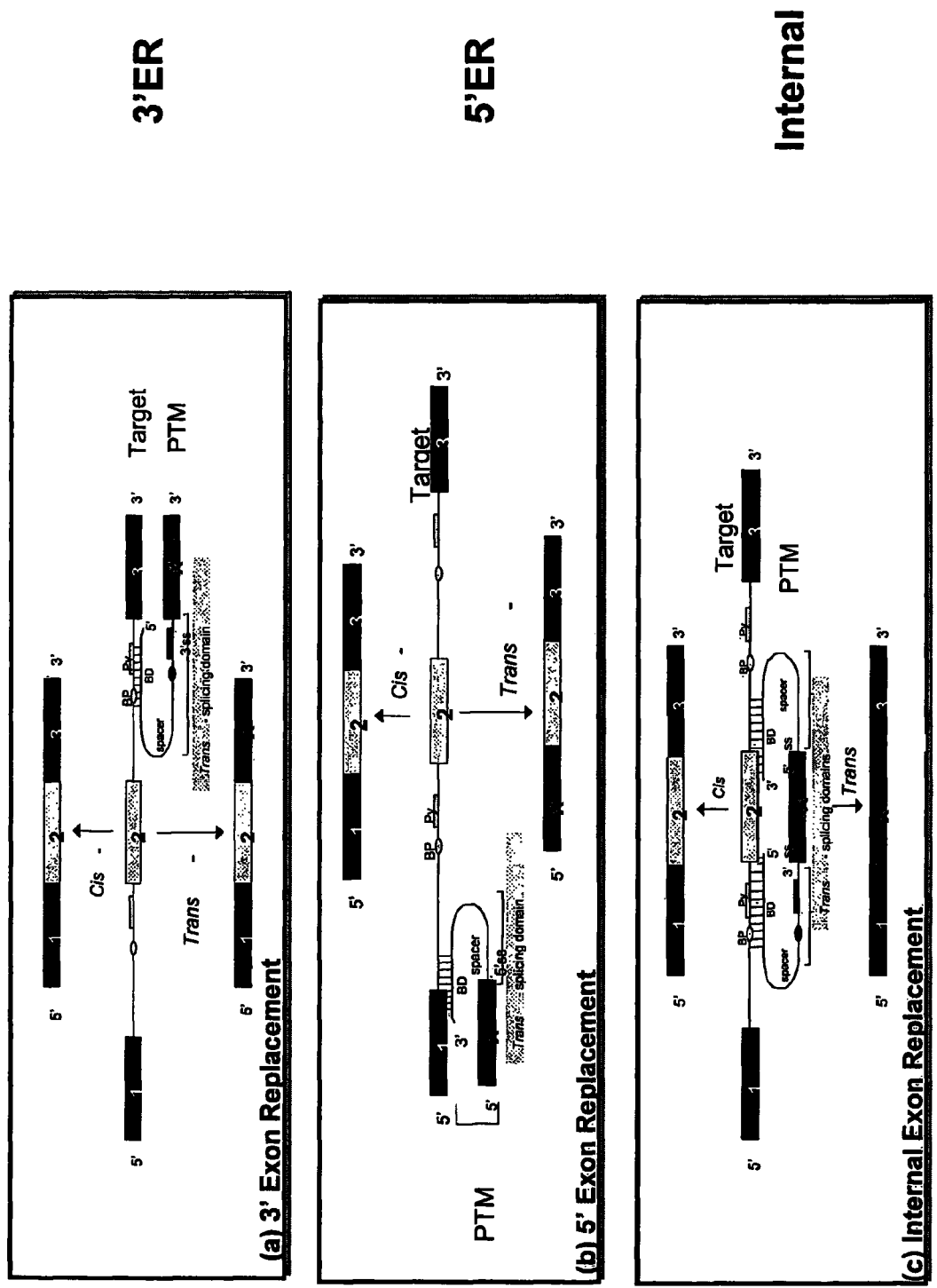
Figure 2:
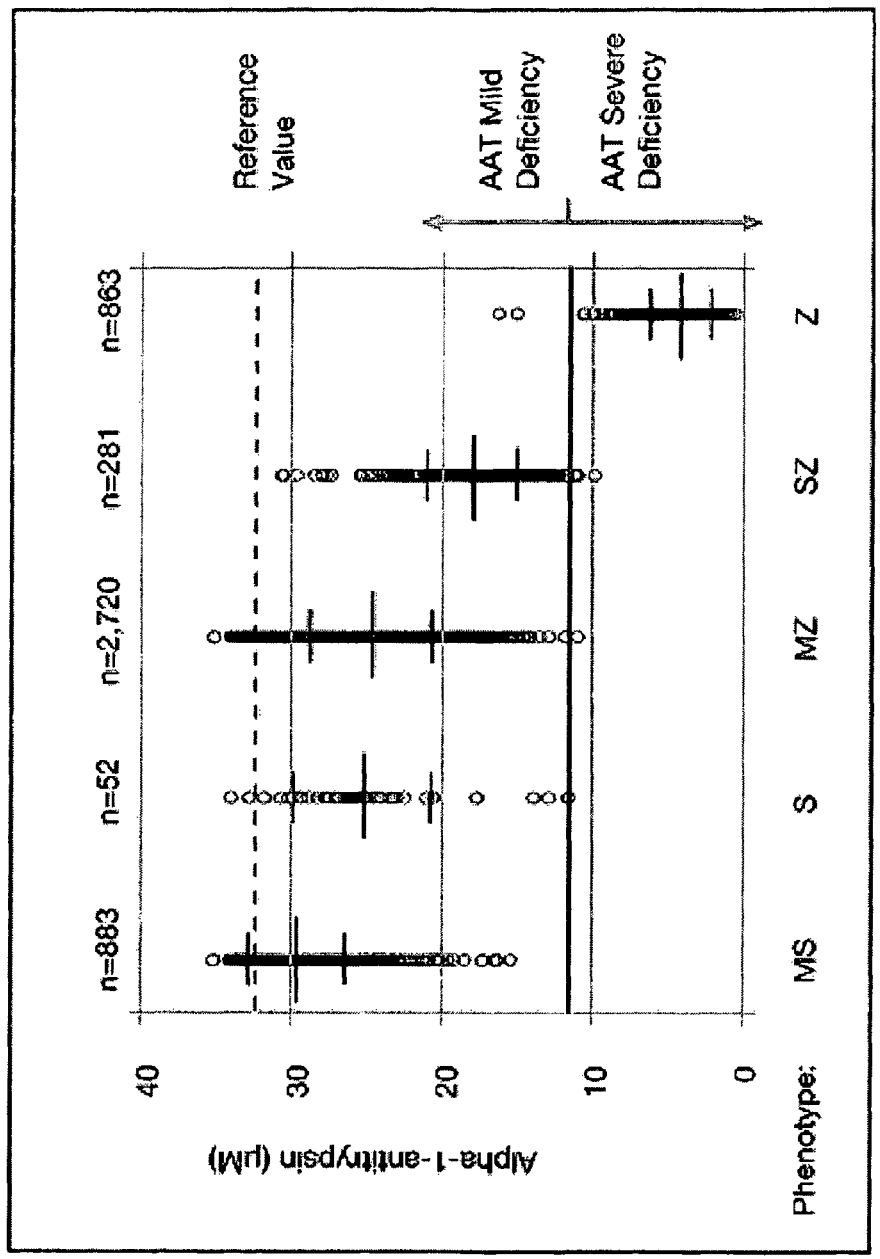
FIG. 2 shows the various phenotypes of inherited protease inhibitor (PI) deficiency.
Figure 3:
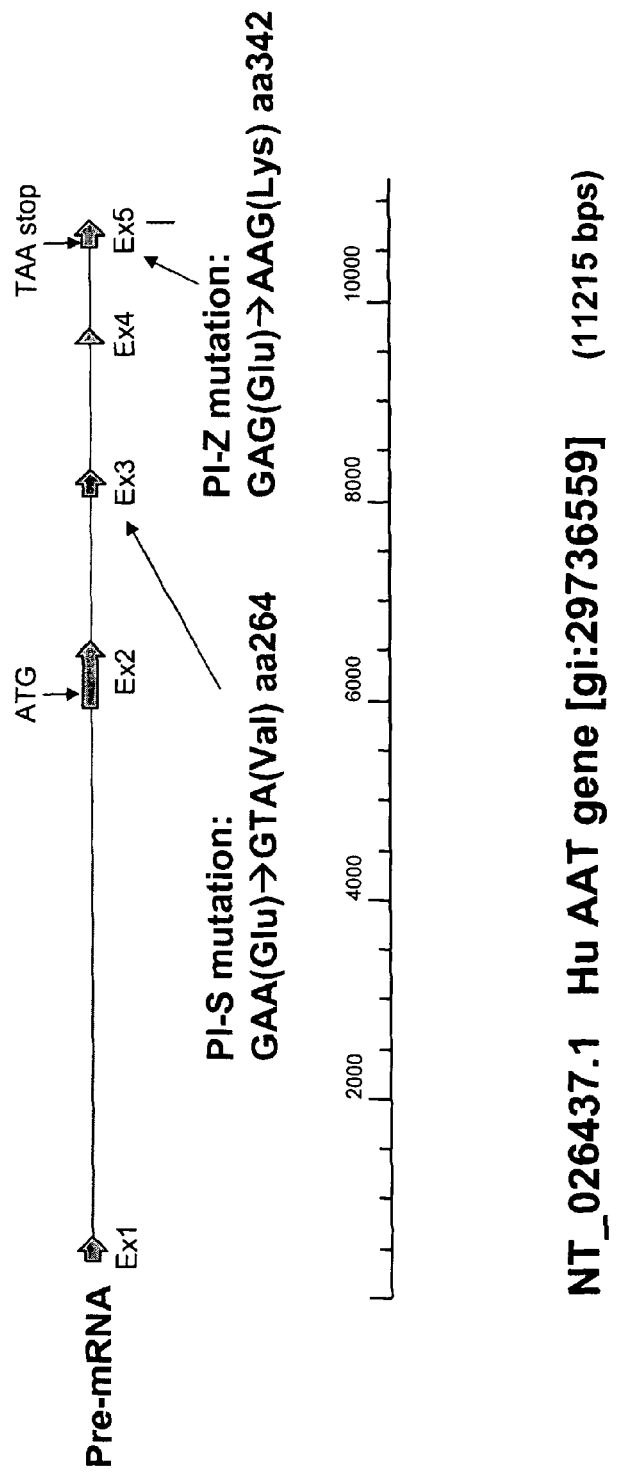
FIG. 3 shows a schematic representation human SERPIN A1 (AAT) gene.
Figure 4:
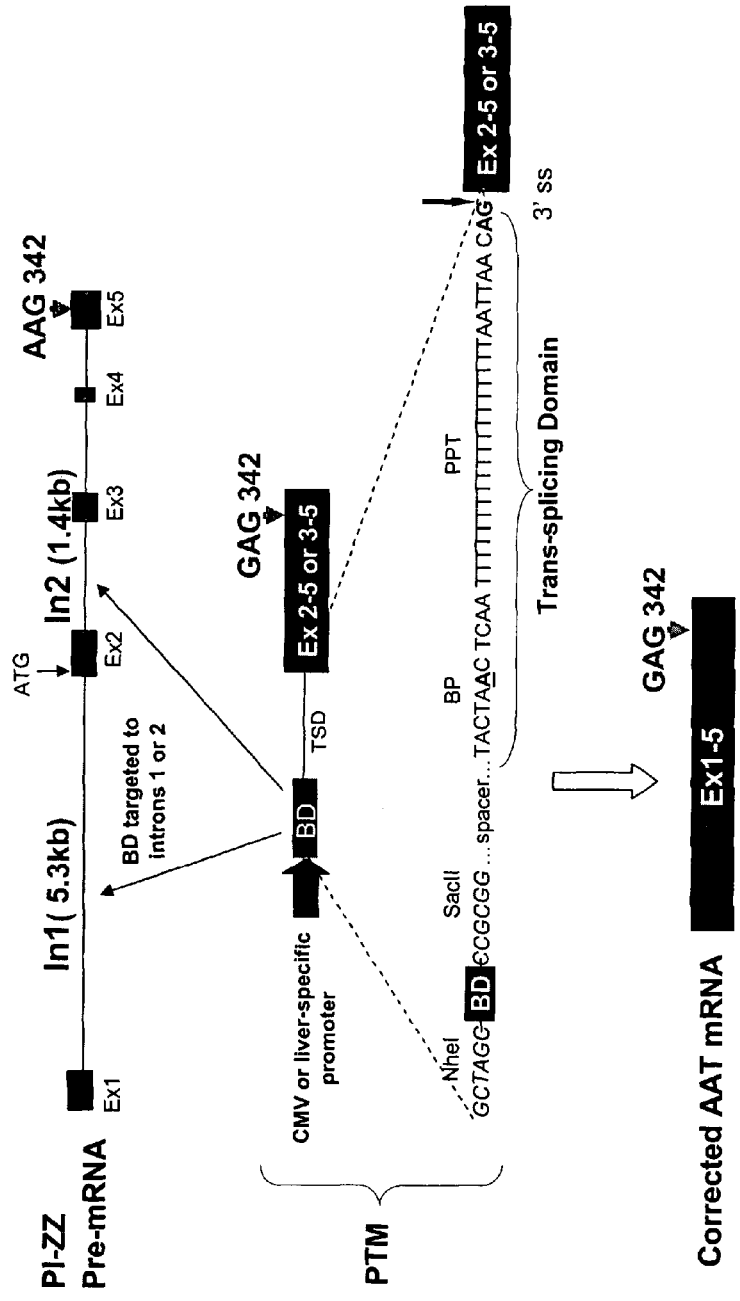
FIG. 4 shows a schematic of Human SERPINA1 pre-mRNA repair using spliceosome mediated trans-splicing (SEQ ID NO: 1-3).
Figure 5:
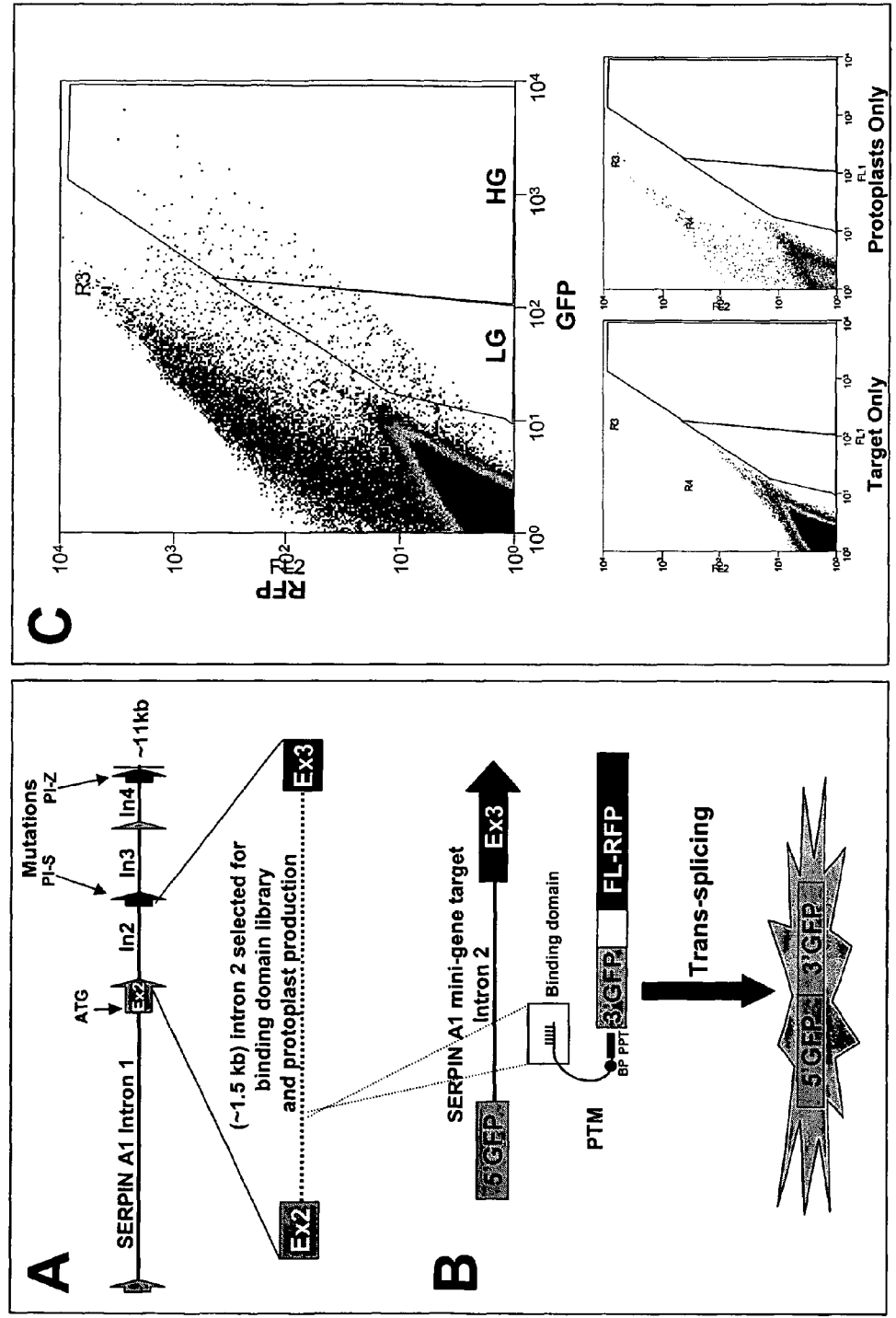

FIG. 5A. shows a schematic of the human SERPIN A1 gene. The positions of the start codon (in exon 2) and the PI-S (in exon 3) and PI-Z (in exon 5) mutations are indicated. Sequences derived from the end of exon 2 through the beginning of exon 3, encompassing all of intron 2, were used in the construction of the binding domain library incorporated into bacterial protoplasts for delivery into target-bearing cells.

FIG. 5B shows a schematic of the proposed trans-splicing reaction. Efficient trans-splicing between the GFP-SERPIN A1 mini-gene target and individual PTMs results in the reconstitution and expression of full length GFP. BP: branch point, PPT: polypyrimidine tract.

FIG. 5C shows a FACS analysis of cells from the SERPIN A1 intron 2 high throughput screen. Cells were collected from both the low (LG) and high (HG) green fractions as indicated (top panel). Corresponding histograms of cells receiving either the SERPIN A1 mini-gene target or protoplasts alone are shown (bottom panels). The "protoplasts only" sample exhibits red fluorescent protein (RFP) expression derived from the PTM itself, in the absence of the target.

Figure 6:
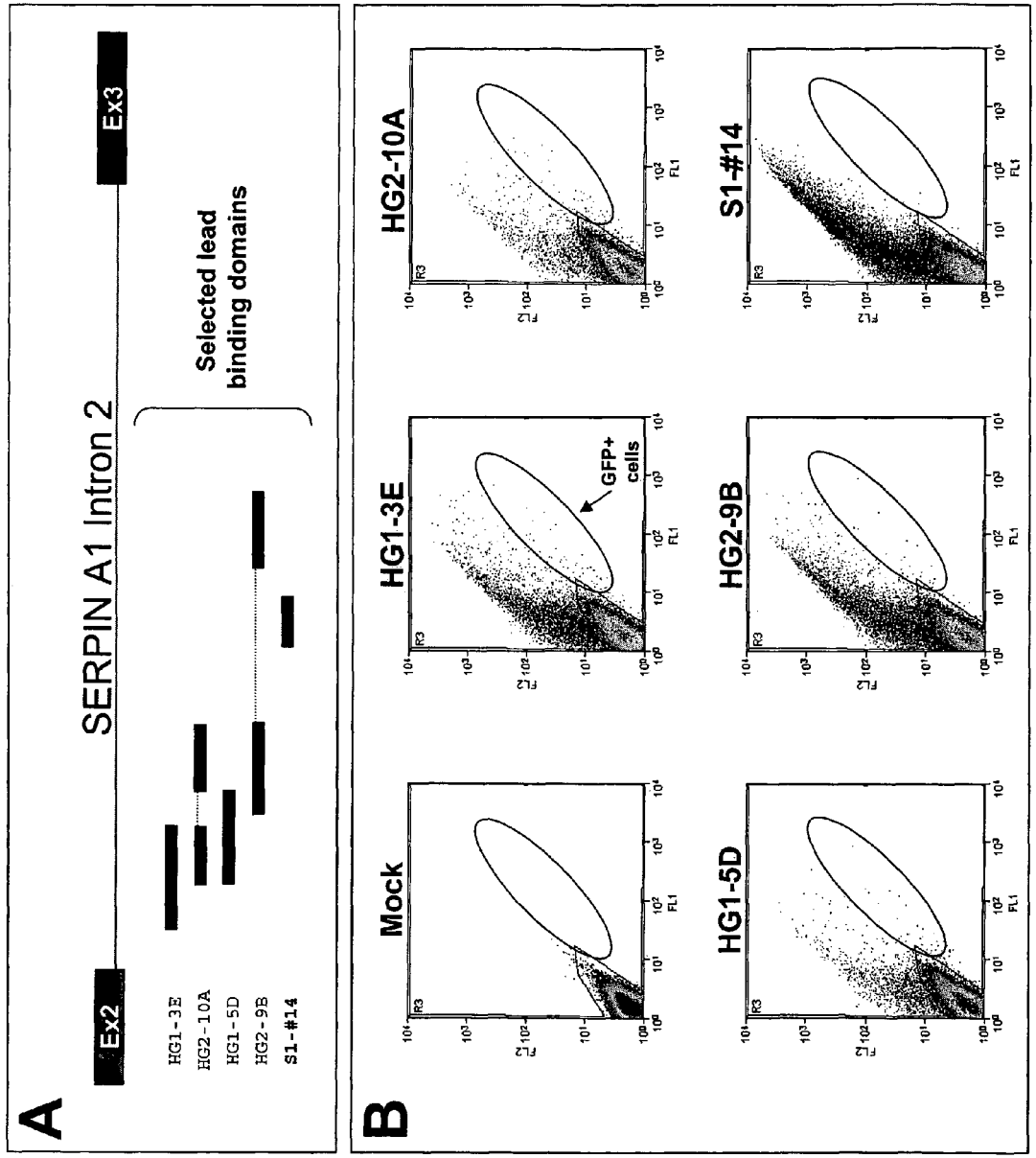

FIG. 6A shows a sequence alignment of binding domains from selected PTMs isolated from the high green (HG) fraction of the SERPIN A1 screen. The sequences align predominantly within the 5' half of the intron. Dashed lines indicate sequence gaps within the respective binding domains.

FIG. 6B shows FACS analysis of various individual lead binding domains illustrated in FIG. 6A. Cells containing an integrated GFP-SERPIN A1 mini-gene target were transfected with plasmids from individual lead PTMs. Cells expressing GFP fluorescence as a result of efficient trans-splicing are indicated by the oval.

FIG. 7A shows a schematic of the binding domains isolated from lead PTMs identified by the screen.

FIG. 7B shows a schematic of lead PTMs identified by the screen that were transferred into the SERPIN A1 correction PTM. The SERPIN A1 PTM is designed to correct both the PI-S and PI-Z mutations and contains modified codon usage (MCU) in exon 3 to differentiate corrected (PI-M) RNA products from endogenous (PI-Z) or contaminating products. Positions of the primers used in the qRT-PCR analysis are shown. PI-S: site of the "S" mutation in exon 3, PI-Z: site of the "Z" mutation in exon 5.

FIG. 7C shows a bar graph of the levels of trans-splicing quantified for each lead PTM in both the GFP (A) and SERPIN A1 (B) contexts. The values for trans-splicing (as molecule numbers per 50 ng total RNA) were normalized against human GAPDH mRNA.

FIG. 8A shows a schematic of various PTMs targeting intron 2. The 3' acceptor AG sequence was modified to AC to disrupt splicing potential in the splicing defective PTMs. Positions of primers used for qRT-PCR analysis are indicated.

FIG. 8B shows a bar graph of the levels of trans-splicing quantified for the two most efficient lead PTMs (HG-13E and HG-29B). The levels are expressed as molecule numbers (per 50 ng total RNA) normalized to human GAPDH mRNA. WT: wild type, SD: splicing defective, M: sequences were modified to eliminate potential cryptic cis-splicing sites within the binding domain.

FIG. 9A shows an agarose gel image of lead SERPINA1 PTMs screened for cryptic cis-splicing. Total RNA was isolated from cells transfected with either a GFP (left) or SERPINA1 (right)-based PTM and the binding domain was amplified by RT-PCR as illustrated (top). Resulting product sizes were compared with products amplified from the corresponding plasmid DNA. Cryptic cis-splicing events are indicated by the arrowheads. Positions of primers used for RT-PCR analysis are indicated. D, DNA sample; R, RNA sample; WT, wild type; SD, splicing defective.

FIG. 9B shows an agarose gel image of modified lead SERPINA1 PTMs screened for cryptic cis-splicing. Total RNA was isolated from cells transfected with a SERPINA1-based PTM and the binding domain was amplified by RT-PCR. Resulting product sizes were compared with products amplified from the corresponding plasmid DNA. Cryptic cis-splicing events are indicated by the arrowheads. D, DNA sample; R, RNA sample; WT, wild type; SD, splicing defective; M, sequences were modified to eliminate potential cryptic cis-splicing sites within the binding domain.

5. DETAILED DESCRIPTION OF THE INVENTION

The present invention relates to novel compositions comprising pre-trans-splicing molecules (PTMs) and the use of such molecules for generating novel nucleic acid molecules. The PTMs of the invention comprise (i) one or more target binding domains that are designed to specifically bind to a SERPINA1 pre-mRNA, (ii) a 3' splice region that includes a branch point, pyrimidine tract, and a 3' splice acceptor site and/or a 5' splice donor site; and (iii) SERPINA1 sequences designed to correct genetic defects in the SERPINA1 RNA. The PTMs of the invention may further comprise sequences that upon processing, yield duplex siRNAs that function to reduce the level of toxic AAT protein within a cell. The PTMs of the invention may also comprise one or more spacer regions that separate the RNA splice site from the target binding domain and/or additional nucleotide sequences such as safety sequences. The methods of the invention encompass contacting the PTMs of the invention with a SERPINA1 target pre-mRNA having genetic defects under conditions in which a portion of the PTM is trans-spliced to a portion of the target pre-mRNA to form a novel chimeric RNA that results in correction of a SERPINA1 genetic defect.

5.1 Structure of the Pre-Trans-Splicing Molecules

The present invention provides compositions for use in generating novel chimeric nucleic acid molecules through targeted RNA trans-splicing. The PTMs of the invention comprise (i) one or more target binding domains that targets binding of the PTM to a SERPINA1 pre-mRNA having a genetic defect (ii) a 3' splice region that includes a branch point, pyrimidine tract and a 3' splice acceptor site and/or 5' splice donor site; and (iii) SERPINA1 exon sequences designed to correct the SERPINA1 genetic defect. The PTMs of the invention may further comprise sequences that upon processing, yield duplex siRNAs that function to reduce the level of toxic AAT protein within a cell.

The PTMs may also include at least one of the following features: (a) binding domains targeted to intron sequences in close proximity to the 3' or 5' splice signals of the target intron, (b) mini introns, (c) ISAR (intronic splicing activator and repressor) consensus binding sites, (d) ribozyme sequences, and/or (e) spacer regions to separate the RNA splice site from the target binding domain.

The general design, construction and genetic engineering of such PTMs and demonstration of their ability to mediate successful trans-splicing reactions within the cell are described in detail in U.S. Pat. Nos. 6,083,702, 6,013,487 and 6,280,978 as well as patent Ser. Nos. 09/941,492, 09/756,095, 09/756,096 and 09/756,097 the disclosures of which are incorporated by reference in their entirety herein.

The general design, construction, and genetic engineering of trans-splicing ribozymes and demonstration of their ability to mediate trans-splicing reactions within the cell are described in detail in U.S. Pat. Nos. 5,667,969, 5,854,038, and 5,869,254, as well as Patent Serial No. 20030036517, the disclosures of which are incorporated by reference in their entirety, herein.

The target binding domain of the PTM endows the PTM with a binding affinity for the target SERPINA1 pre-mRNA. As used herein, a target binding domain is defined as any molecule, i.e., nucleotide, protein, chemical compound, etc., that confers specificity of binding and anchors the pre-mRNA closely in space to the PTM so that the spliceosome processing machinery of the nucleus can trans-splice a portion of the PTM to a portion of the pre-mRNA.

The target binding domain of the PTM may contain multiple binding domains which are complementary to and in anti-sense orientation to the targeted region of the selected SERPINA1 pre-mRNA. The target binding domains may comprise up to several thousand nucleotides. In preferred embodiments of the invention the binding domains may comprise at least 10 to 30 and up to several hundred or more nucleotides. The efficiency and/or specificity of the PTM may be increased significantly by increasing the length of the target binding domain (Puttaraju et al., 2001, Mol. Ther. 4:105-114). For example, the target binding domain may comprise several hundred nucleotides, or more. In addition, although the target binding domain may be "linear" it is understood that the RNA will very likely fold to form a secondary "safety" structure that may sequester the PTM splice site(s) until the PTM encounters its pre-mRNA target, thereby increasing the specificity and efficiency of the intended splicing reaction. A second target binding region may be placed at the 3' end of the molecule and can be incorporated into the PTM of the invention. Absolute complementarily, although preferred, is not required. A sequence "complementary" to a portion of an RNA, as referred to herein, means a sequence having sufficient complementarity to be able to hybridize with the target pre-mRNA, forming a stable duplex. The ability to hybridize will depend on both the degree of complementarity and the length of the nucleic acid (See, for example, Sambrook et al., 1989, *Molecular Cloning, A Laboratory Manual,* 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

Binding domains may encompass any or all sequences located within the target intron and flanking exons and may consist of contiguous sequence or contain sequence gaps ranging in size from a few to several hundred nucleotides in length (e.g. human SERPINA1 leads HG2-9B and HG2-10A as shown in Table 1). In such cases, the binding domain may be considered to be comprised of multiple, smaller binding domains that are positioned within the PTM in either orientation (sense or antisense) relative to the target sequence or to each other. Any or all sequence elements within the binding domain may contain significant complementarity to the target region.

Depending on the length of the intron, lead binding domains may be clustered predominantly within the 5' region and may be grouped into overlapping clusters (e.g. HPV leads from the high capacity screen patent or SERPINA1 leads illustrated in FIG. 6A). While the average size of lead binding domains (e.g. for SERPINA1) is less than 200 nucleotides in length, longer sequences have been identified and may improve trans-splicing efficiency by providing greater complementarity to the target region (e.g. HG1-3E and HG2-10A) or may fold into defined structural elements (i.e. natural "safety" structures, hairpins, etc) that may prevent non-specific trans-splicing and, in effect, promote more efficient trans-splicing with the desired target.

Binding may also be achieved through other mechanisms, for example, through triple helix formation, aptamer interactions, antibody interactions or protein/nucleic acid interactions such as those in which the PTM is engineered to recognize a specific RNA binding protein, i.e., a protein bound to a specific target pre-mRNA. Alternatively, the PTMs of the invention may be designed to recognize secondary structures, such as for example, hairpin structures resulting from intramolecular base pairing between nucleotides within an RNA molecule.

In a specific embodiment of the invention, the target binding domain is complementary and in anti-sense orientation to sequences in close proximity to the region of the SERPINA1 target pre-mRNA targeted for trans-splicing.

The PTM molecule also contains a 3' splice region that includes a branch point sequence and a 3' splice acceptor AG site and/or a 5' splice donor site. The 3' splice region may further comprise a polypyrimidine tract. Consensus sequences for the 5' splice donor site and the 3' splice region used in RNA splicing are well known in the art (See, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and /=the splice site) (SEQ ID NO:4). The 3' splice site consists of three separate sequence elements: the branch point or branch site, a polypyrimidine tract and the 3' consensus sequence (YAG). The branch point consensus sequence in mammals is YNYURAC (Y=pyrimidine; N=any nucleotide) (SEQ ID NO:5). The underlined A is the site of branch formation. A polypyrimidine tract is located between the branch point and the splice site acceptor and is important for different branch point utilization and 3' splice site recognition. Recently, pre-mRNA introns beginning with the dinucleotide AU and ending with the dinucleotide AC have been identified and referred to as U12 introns. U12 intron sequences as well as any sequences that function as splice acceptor/donor sequences may also be used to generate the PTMs of the invention.

A spacer region to separate the RNA splice site from the target binding domain may also be included in the PTM. The spacer region may be designed to include features such as stop codons which would block any translation of an unspliced PTM and/or sequences that enhance trans-splicing to the target pre-mRNA.

In a preferred embodiment of the invention, a "safety" is also incorporated into the spacer, binding domain, or elsewhere in the PTM to prevent non-specific trans-splicing (Puttaraju et al., 1999. Nat. Biotech. 17:246-252; Mansfield, S G et al., 2000. Gene Therapy 7:1885-1895). This is a region of the PTM that covers elements of the 3' and/or 5' splice site of the PTM by relatively weak complementarity, preventing non-specific trans-splicing. The PTM is designed in such a way that upon hybridization of the binding/targeting portion(s) of the PTM, the 3' and/or 5' splice site is uncovered and becomes fully active.

The "safety" consists of one or more complementary stretches of cis-sequence (or could be a second, separate, strand of nucleic acid) which binds to one or both sides of the PTM branch point, pyrimidine tract, 3' splice site and/or 5' splice site (splicing elements), or could bind to parts of the splicing elements themselves. This "safety" binding prevents the splicing elements from being active (i.e. block U2 snRNP or other splicing factors from attaching to the PTM splice site recognition elements). The binding of the "safety" may be disrupted by the binding of the target binding region of the PTM to the target pre-mRNA, thus exposing and activating the PTM splicing elements (making them available to trans-splice into the target pre-mRNA).

A nucleotide sequence encoding a translatable protein capable of restoring AAT activity is also included in the PTM of the invention. The most severe form of AAT deficiency occurs in subjects who are homozygous for a single base change (GAG→AAG) at amino acid residue 342 in exon 5 of the SERPINA1 gene (NCBI OMIM 107400). A less severe mutation results from a single base change (GAA→GTA) at amino acid residue 264 in exon 3 of the SERPINA1 gene (NCBI OMIM 107400). Thus, the PTMs of the invention may be designed to replace either exon 3 or exon 5, exons 2-5, exons 3-5, or exons 4-5, depending on the type of trans-splicing reaction and binding domains used.

A variety of different PTM molecules may be synthesized for use in the production of a novel chimeric RNA which complements a defective or inactive SERPINA1 protein. The PTMs of the invention may contain SERPINA1 exon sequences which when trans-spliced to the SERPINA1 target pre-mRNA will result in the formation of a composite or chimeric RNA capable of encoding a functional SERPINA1 protein. The nucleotide sequence of the SERPINA1 gene, on human chromosome 14q32.1, is known and incorporated herein in its entirety (NCBI gi: 21361197; LocusID: 5265; SERPINA1 lies within Contig NT_026437 (pos. 74775565-74764351)).

The SERPINA1 exon sequences to be included in the structure of the PTM will depend on the specific SERPINA1 mutation targeted for correction. For example, when targeting correction of a mutation in SERPINA1 exon 3 or exon 5, the PTM will be designed to include at least the exon sequences in need of repair. In an embodiment of the invention, 3' exon replacement will result in the formation of a chimeric RNA molecule that encodes for a functional SERPINA1 protein. The PTM's of the invention may be engineered to contain a single SERPINA1 exon sequence, multiple SERPINA1 exon sequences, or alternatively the complete set of 4 SERPINA1 exon sequences (exons 2-5). The number and identity of the SERPINA1 sequences to be used in the PTMs will depend on the targeted SERPINA1 mutation, and the type of trans-splicing reaction, i.e., 5' exon replacement, 3' exon replacement or internal exon replacement that will occur. The formation of a corrected SERPINA1 transcript will result in synthesis of normal AAT protein, thereby elevating blood levels of normal protein which helps to protect the lung from protease destruction. In addition, correction of SERPINA1 defects in liver cells reduces the load of toxic defective AAT protein accumulation in such cells, thereby reducing the risk of liver disease.

In addition, PTMs may incorporate sequences encoding hairpins that are cleaved by processing endonucleases, including Dicer, to yield in the cytoplasm mature ~21-23 bp duplex siRNAs directed specifically against the PI-ZZ SERPINA1 mRNA ((GAG→AAG) at amino acid residue 342). By degrading the defective PI-ZZ mRNA, the siRNAs will reduce the level of defective AAT protein, and provide additional protection against the cytotoxic accumulation of defective AAT protein. The precursor sequences to the siRNA can be encoded, for example, within an intron of the PTM, or within the trans-splicing domain of the PTM. Because an appreciable level of unspliced PTM reaches the cytoplasm, the latter approach may provide higher levels of final siRNA than the former. In a specific embodiment of the invention, the siRNA can be targeted specifically against the defective (PI-Z) SERPINA1 mRNA, sparing normal (PI-M) SERPINA1 mRNA, by incorporating isocodon substitutions into the PTM exons that are used to replace the defective mRNA. The PTM can also encode sequences that function as anti-sense or that trigger RNAi effects by forming double stranded structures (including the 21-23 nucleotide double strands that trigger RNAi) between the PTM and the endogenous mutant form of the AAT gene.

The present invention further provides PTM molecules wherein the coding region of the PTM is engineered to contain mini-introns. The insertion of mini-introns into the coding sequence of the PTM is designed to increase definition of the exon and enhance recognition of the PTM acceptor site. Mini-intron sequences to be inserted into the coding regions of the PTM include small naturally occurring introns or, alternatively, any intron sequences, including synthetic mini-introns, which include 5' consensus donor sites and 3' consensus acceptor sequences which include a branch point, a 3' splice site and in some instances a pyrimidine tract.

The mini-intron sequences are preferably between about 60-150 nucleotides in length, however, mini-intron sequences of increased lengths may also be used. In a preferred embodiment of the invention, the mini-intron comprises the 5' and 3' end of an endogenous intron. In a specific embodiment of the invention, the mini-intron sequences may be designed to express or act as duplex siRNA as described above.

In a specific embodiment of the invention, an intron of 528 nucleotides comprising the following sequences may be utilized. Sequence of the intron construct is as follows:

```
5' fragment sequence (SEQ ID NO: 6):
Gtagttcttttgttcttcactattaagaacttaatttggtgtccatgtct
cttttttttttctagtttgtagtgctggaaggtattttggagaaattctt
acatgagcattaggagaatgtatgggtgtagtgtcttgtataatagaaat
tgttccactgataatttactctagttttttatttcctcatattattttca
gtggcttttcttccacatctttatattttgcaccacattcaacactgta
gcggccgc.

3' fragment sequence (SEQ ID NO: 7):
Ccaactatctgaatcatgtgccccttctctgtgaacctctatcataatac
ttgtcacactgtattgtaattgtctcttttacttttccttgtatcttttg
tgcatagcagagtacctgaaacaggaagtattttaaatattttgaatcaa
atgagttaatagaatctttacaaataagaatatacacttctgcttaggat
gataattggaggcaagtgaatcctgagcgtgatttgataatgacctaata
atgatgggttttatttccag.
```

In an embodiment of the invention, the Tia-1 binding sequences are inserted within 100 nucleotides from the 5' donor site. In a preferred embodiment of the invention, the Tia-1 binding sequences are inserted within 50 nucleotides from the 5' donor site. In a more preferred embodiment of the invention, ISAR sequences (Jones et al., 2001. NAR 29:3557-3565) are inserted within 20 nucleotides of the 5' donor site.

The compositions of the invention further comprise PTMs that have been engineered to include cis-acting ribozyme sequences. The inclusion of such sequences is designed to reduce PTM translation in the absence of trans-splicing or to produce a PTM with a specific length or defined end(s). The ribozyme sequences that may be inserted into the PTMs include any sequences that are capable of mediating a cis-acting (self-cleaving) RNA splicing reaction. Such ribozymes include but are not limited to hammerhead, hairpin and hepatitis delta virus ribozymes (see, Chow et al. 1994, *J Biol Chem* 269:25856-64). The ribozyme sequence can also be targeted to destroy the endogenous mutant form of AAT.

In an embodiment of the invention, splicing enhancers such as, for example, sequences referred to as exonic splicing enhancers may also be included in the PTM design. Trans-acting splicing factors, namely the serine/arginine-rich (SR) proteins, have been shown to interact with such exonic splicing enhancers and modulate splicing (See, Tacke et al., 1999, *Curr. Opin. Cell Biol.* 11:358-362; Tian et al., 2001, *J. Biological Chemistry* 276:33833-33839; Fu, 1995, *RNA* 1:663-680). Nuclear localization signals may also be included in the PTM molecule (Dingwell and Laskey, 1986, *Ann. Rev. Cell Biol.* 2:367-390; Dingwell and Laskey, 1991, *Trends in Biochem. Sci.* 16:478-481). Such nuclear localization signals can be used to enhance the transport of synthetic PTMs into the nucleus where trans-splicing occurs.

Additional features can be added to the PTM molecule either after, or before, the nucleotide sequence encoding a translatable protein, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the PTM structure to prevent translation of unspliced PTMs. Further elements such as a 3' hairpin structure, circularized RNA, nucleotide base modification, or synthetic analogs can be incorporated into PTMs to promote or facilitate nuclear localization and spliceosomal incorporation, and intra-cellular stability.

In addition to specific promoter/enhancer sequences or polyadenylation signals, other sequence and/or structural elements may be incorporated into the PTM to increase the stability of the PTM, prevent decay of either the PTM or the trans-spliced message, promote trafficking of the trans-spliced molecule into the cytoplasm for efficient translation, or promote or enhance translation of the trans-spliced product. Such elements may be positioned within the 3' untranslated region (3'UTR) of the PTM molecule and include alternative polyadenylation (hexanucleotide) signals or structures such as a 3' hairpin, specific AU-rich sequence elements (a subset which are known to enhance mRNA stability) and/or other RNA recognition motifs or repetitive elements that promote interactions with trans-acting factors (such as hnRNP D isoforms that inhibit mRNA decay (Xu N. et al. 2001. Versatile role for hnRNP D isoforms in the differential regulation of cytoplasmic mRNA turnover. Mol. Cell. Biol. 21(20):6960-6971); for additional reviews see Wilusz C. J. et al. 2001. Cap-to-tail guide to mRNA turnover. Nature Reviews 2:237-246; Day, D. A. and Tuite, M. F. 1998. Post-transcriptional gene regulatory mechanisms in eukaryotes: an overview. Journal of Endocrinology 157:361-371; Mignone F., et al. 2002, Untranslated regions of mRNAs, Genome Biol. 3(3):reviews0004.1-reviews0004.10).

PTMs may also be generated that require a double-trans-splicing reaction for generation of a chimeric trans-spliced product. Such PTMs could, for example, be used to replace the internal exon 3 of the SERPINA1 gene. PTMs designed to promote two trans-splicing reactions are engineered as described above, however, they contain both 5' donor sites and 3' splice acceptor sites. In addition, the PTMs may comprise two or more binding domains.

Optimal PTMs for defective SERPINA1 pre-mRNA targets may be selected using high-capacity screens. Such screens include, but are not limited to, those described in patent application Ser. No. 10/693,192. Briefly, a PTM library is constructed of binding domains complementary to sequences of the SERPINA1 pre-mRNA target. The exonic region of the PTM contains a sequence encoding a C-terminal portion of green fluorescent protein (GFP) reporter gene that is incapable of generating fluorescence. The PTM library is delivered clonally into readily transfectable mammalian cells, such as COS7 or 293T cells, preferably cells expressing SV40T antigen, by transfection of bacterial protoplasts containing the PTM vector or with viral vectors encoding the PTMs. A target vector is prepared encoding a 5'GFP-SERPINA1 synthetic target pre-mRNA, where a 5'GFP sequence encodes the portion of the ZsGreen open reading frame that is missing from the PTM, itself followed by sequence encoding the SERPINA1 pre-mRNA target sequence.

Approximately 24-48 hours after transfecting the PTM vector, the target vector is transfected into the same cell, using Lipofectamine reagents or other optimal methods of transfection, and the cells are analyzed by FACS for expression of GFP fluorescence. Correct trans-splicing occurring between the PTM RNA and the synthetic target pre-mRNA target reconstitutes an mRNA encoding fluorescent GFP protein. Total RNA samples from transfected cells may be prepared and analyzed for the efficiency of trans-splicing, by quantitative real-time PCR (qRT-PCR) using target- and PTM-specific primers. By scoring the level of GFP fluorescence, one can identify the most efficiently trans-splicing PTMs in a population of PTMs containing different BDs and TSDs. By comparing the correctly trans-spliced and repaired RNA product with the level of cis-spliced product generated by splicing within the target pre-mRNA itself, one can quantitate the efficiency of the trans-splicing reaction for any individual PTM. Once optimal BDs and TSDs are identified, these sequences are readily transferred into a SERPINA1 PTM cassette appropriate for trans-splicing to the SERPINA1 gene endogenous to a cell, such as a hepatocyte, for repair of the endogenous SERPINA1 pre-mRNA in the liver.

When specific PTMs are to be synthesized in vitro (synthetic PTMs), such PTMs can be modified at the base moiety, sugar moiety, or phosphate backbone, for example, to improve stability of the molecule, hybridization to the target SERPINA1 mRNA, transport into the cell, etc. For example, modification of a PTM to reduce the overall charge can enhance the cellular uptake of the molecule. In addition modifications can be made to reduce susceptibility to nuclease or chemical degradation. The nucleic acid molecules may be synthesized in such a way as to be conjugated to another molecule such as a peptides (e.g., for targeting host cell receptors in vivo), or an agent facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci.* 84:648-652; PCT Publication No. W088/09810, published Dec. 15, 1988) or the blood-brain barrier (see, e.g., PCT Publication No. W089/10134, published Apr. 25, 1988), hybridization-triggered cleavage agents (see, e.g., Krol et al., 1988, *BioTechniques* 6:958-976) or intercalating agents (see, e.g., Zon, 1988, *Pharm. Res.* 5:539-549). To this end, the nucleic acid molecules may be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing intracellular stability and half-life. Possible modifications include, but are not limited to, the addition of flanking sequences of ribonucleotides to the 5' and/or 3' ends of the molecule. In some circumstances where increased stability is desired, nucleic acids having modified internucleoside linkages such as 2'-0-methylation may be preferred. Nucleic acids containing modified internucleoside linkages may be synthesized using reagents and methods that are well known in the art (see, Uhlmann et al., 1990, *Chem. Rev.* 90:543-584; Schneider et al., 1990, Tetrahedron Lett. 31:335 and references cited therein).

The synthetic PTMs of the present invention are preferably modified in such a way as to increase their stability in the cells. Since RNA molecules are sensitive to cleavage by cellular ribonucleases, it may be preferable to use as the competitive inhibitor a chemically modified oligonucleotide (or combination of oligonucleotides) that mimics the action of the RNA binding sequence but is less sensitive to nuclease cleavage. In addition, the synthetic PTMs can be produced as nuclease resistant circular molecules with enhanced stability to prevent degradation by nucleases (Puttaraju et al., 1995, *Nucleic Acids Symposium Series No.* 33:49-51; Puttaraju et al., 1993, *Nucleic Acid Research* 21:4253-4258). Other modifications may also be required, for example to enhance binding, to enhance cellular uptake, to improve pharmacology or pharmacokinetics or to improve other pharmaceutically desirable characteristics.

Modifications, which may be made to the structure of the synthetic PTMs include but are not limited to backbone modifications such as use of:

(i) phosphorothioates (X or Y or W or Z=S or any combination of two or more with the remainder as O). e.g. Y=S (Stein, C. A., et al., 1988, *Nucleic Acids Res.*, 16:3209-3221), X=S (Cosstick, R., et al., 1989, *Tetrahedron Letters*, 30, 4693-4696), Y and Z=S (Brill, W. K.-D., et al., 1989, *J. Amer. Chem. Soc.*, 111:2321-2322); (ii) methylphosphonates (e.g. Z=methyl (Miller, P. S., et al., 1980, *J. Biol. Chem.*, 255:9659-9665); (iii) phosphoramidates (Z=N-(alkyl)$_2$ e.g. alkyl methyl, ethyl, butyl) (Z=morpholine or piperazine) (Agrawal, S., et al., 1988, *Proc. Natl. Acad. Sci. USA* 85:7079-7083) (X or W=NH) (Mag, M., et al., 1988, *Nucleic Acids Res.*, 16:3525-3543); (iv) phosphotriesters (Z=O-alkyl e.g. methyl, ethyl, etc) (Miller, P. S., et al., 1982, *Biochemistry*, 21:5468-5474); and (v) phosphorus-free linkages (e.g. carbamate, acetamidate, acetate) (Gait, M. J., et al., 1974, *J. Chem. Soc. Perkin I*, 1684-1686; Gait, M. J., et al., 1979, *J. Chem. Soc. Perkin I*, 1389-1394).

In addition, sugar modifications may be incorporated into the PTMs of the invention. Such modifications include the use of: (i) 2'-ribonucleosides (R=H); (ii) 2'-O-methylated nucleosides (R=OMe) (Sproat, B. S., et al., 1989, *Nucleic Acids Res.*, 17:3373-3386); and (iii) 2'-fluoro-2'-riboxynucleosides (R=F) (Krug, A., et al., 1989, *Nucleosides and Nucleotides*, 8:1473-1483).

Further, base modifications that may be made to the PTMs, including but not limited to use of: (i) pyrimidine derivatives substituted in the 5-position (e.g. methyl, bromo, fluoro etc) or replacing a carbonyl group by an amino group (Piccirilli, J. A., et al., 1990, *Nature*, 343:33-37); (ii) purine derivatives lacking specific nitrogen atoms (e.g. 7-deaza adenine, hypoxanthine) or functionalized in the 8-position (e.g. 8-azido adenine, 8-bromo adenine) (for a review see Jones, A. S., 1979, *Int. J. Biolog. Macromolecules*, 1:194-207).

In addition, the PTMs may be covalently linked to reactive functional groups, such as: (i) psoralens (Miller, P. S., et al., 1988, *Nucleic Acids Res.*, Special Pub. No. 20, 113-114), phenanthrolines (Sun, J-S., et al., 1988, *Biochemistry*, 27:6039-6045), mustards (Vlassov, V. V., et al., 1988, *Gene*, 72:313-322) (irreversible cross-linking agents with or without the need for co-reagents); (ii) acridine (intercalating agents) (Helene, C., et al., 1985, *Biochimie*, 67:777-783); (iii) thiol derivatives (reversible disulphide formation with proteins) (Connolly, B. A., and Newman, P. C., 1989, *Nucleic Acids Res.*, 17:4957-4974); (iv) aldehydes (Schiffs base formation); (v) azido, bromo groups (UV cross-linking); or (vi) ellipticines (photolytic cross-linking) (Perrouault, L., et al., 1990, *Nature*, 344:358-360).

In an embodiment of the invention, oligonucleotide mimetics in which the sugar and internucleoside linkage, i.e., the backbone of the nucleotide units, are replaced with novel groups can be used. For example, one such oligonucleotide mimetic which has been shown to bind with a higher affinity to DNA and RNA than natural oligonucleotides is referred to as a peptide nucleic acid (PNA) (for review see, Uhlmann, E. 1998, Biol. Chem. 379:1045-52). Thus, PNA may be incorporated into synthetic PTMs to increase their stability and/or binding affinity for the target pre-mRNA.

In another embodiment of the invention synthetic PTMs may covalently linked to lipophilic groups or other reagents capable of improving uptake by cells. For example, the PTM molecules may be covalently linked to: (i) cholesterol (Letsinger, R. L., et al., 1989, *Proc. Natl. Acad. Sci. USA*, 86:6553-6556); (ii) polyamines (Lemaitre, M., et al., 1987, *Proc. Natl. Acad. Sci, USA*, 84:648-652); other soluble polymers (e.g. polyethylene glycol) to improve the efficiently with which the PTMs are delivered to a cell. In addition, combinations of the above identified modifications may be utilized to increase the stability and delivery of PTMs into the target cell. The PTMs of the invention can be used in methods designed to produce a novel chimeric RNA in a target cell.

The methods of the present invention comprise delivering to the target cell a PTM which may be in any form used by one skilled in the art, for example, an RNA molecule, or a DNA vector which is transcribed into a RNA molecule, wherein said PTM binds to a pre-mRNA and mediates a trans-splicing reaction resulting in formation of a chimeric RNA comprising a portion of the PTM molecule spliced to a portion of the pre-mRNA.

In a specific embodiment of the invention, the PTMs of the invention can be used in methods designed to produce a novel chimeric RNA in a target cell so as to result in correction of AAT defects. The methods of the present invention comprise delivering to a cell a PTM which may be in any form used by one skilled in the art, for example, an RNA molecule, or a DNA vector which is transcribed into a RNA molecule, wherein said PTM binds to a mutant SERPINA1 pre-mRNA and mediates a trans-splicing reaction resulting in formation of a chimeric RNA comprising a portion of the PTM molecule spliced to a portion of the pre-mRNA.

5.2 Synthesis of the Trans-Splicing Molecules

The nucleic acid molecules of the invention can be RNA or DNA or derivatives or modified versions thereof, single-stranded or double-stranded. By nucleic acid is meant a PTM molecule or a nucleic acid molecule encoding a PTM molecule, whether composed of deoxyribonucleotides or ribonucleotides, and whether composed of phosphodiester linkages or modified linkages. The term nucleic acid also specifically includes nucleic acids composed of bases other than the five biologically occurring bases (adenine, guanine, thymine, cytosine and uracil). In addition, the PTMs of the invention may comprise DNA/RNA, RNA/protein or DNA/RNA/protein chimeric molecules that are designed to enhance the stability of the PTMs.

The PTMs of the invention can be prepared by any method known in the art for the synthesis of nucleic acid molecules. For example, the nucleic acids may be chemically synthesized using commercially available reagents and synthesizers by methods that are well known in the art (see, e.g., Gait, 1985, *Oligonucleotide Synthesis: A Practical Approach*, IRL Press, Oxford, England).

Alternatively, synthetic PTMs can be generated by in vitro transcription of DNA sequences encoding the PTM of interest. Such DNA sequences can be incorporated into a wide variety of vectors downstream from suitable RNA polymerase promoters such as the T7, SP6, or T3 polymerase promoters. Consensus RNA polymerase promoter sequences include the following:

```
T7:  TAATACGACTCACTATAGGGAGA     (SEQ ID NO:  8)

SP6: ATTTAGGTGACACTATAGAAGNG     (SEQ ID NO:  9)

T3:  AATTAACCCTCACTAAAGGGAGA.    (SEQ ID NO: 10)
```

The base in bold is the first base incorporated into RNA during transcription. The underline indicates the minimum sequence required for efficient transcription.

RNAs may be produced in high yield via in vitro transcription using plasmids such as SPS65 and Bluescript (Promega Corporation, Madison, Wis.). In addition, RNA amplification methods such as Q-β amplification can be utilized to produce the PTM of interest.

The PTMs may be purified by any suitable means, as are well known in the art. For example, the PTMs can be purified by gel filtration, affinity or antibody interactions, reverse phase chromatography or gel electrophoresis. Of course, the skilled artisan will recognize that the method of purification will depend in part on the size, charge and shape of the nucleic acid to be purified.

The PTM's of the invention, whether synthesized chemically, in vitro, or in vivo, can be synthesized in the presence of modified or substituted nucleotides to increase stability, uptake or binding of the PTM to a target pre-mRNA. In addition, following synthesis of the PTM, the PTMs may be modified with peptides, chemical agents, antibodies, or nucleic acid molecules, for example, to enhance the physical properties of the PTM molecules. Such modifications are well known to those of skill in the art.

In instances where a nucleic acid molecule encoding a PTM is utilized, cloning techniques known in the art may be used for cloning of the nucleic acid molecule into an expression vector. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

The DNA encoding the PTM of interest may be recombinantly engineered into a variety of host vector systems that also provide for replication of the DNA in large scale and contain the necessary elements for directing the transcription of the PTM. The use of such a construct to transfect target cells in the patient will result in the transcription of sufficient amounts of PTMs that will form complementary base pairs with the endogenously expressed pre-mRNA targets, such as for example, SERPINA1 pre-mRNA target, and thereby facilitate a trans-splicing reaction between the complexed nucleic acid molecules. For example, a vector can be introduced in vivo such that it is taken up by a cell and directs the transcription of the PTM molecule. Such a vector can remain episomal or become chromosomally integrated, as long as it can be transcribed to produce the desired RNA, i.e., PTM. Such vectors can be constructed by recombinant DNA technology methods standard in the art.

Vectors encoding the PTM of interest can be plasmid, viral, or others known in the art, used for replication and expression in mammalian cells. Expression of the sequence encoding the PTM can be regulated by any promoter/enhancer sequences known in the art to act in mammalian, preferably human cells. Such promoters/enhancers can be inducible or constitutive. Such promoters include but are not limited to: the SV40 early promoter region (Benoist, C. and Chambon, P. 1981, *Nature* 290:304-310), the promoter contained in the 3' long terminal repeat of Rous sarcoma virus (Yamamoto et al., 1980, *Cell* 22:787-797), the herpes thymidine kinase promoter (Wagner et al., 1981, *Proc. Natl. Acad. Sci. U.S.A.* 78:14411445), the regulatory sequences of the metallothionein gene (Brinster et al., 1982, *Nature* 296:39-42), the viral CMV promoter, the human chorionic gonadotropin-β promoter (Hollenberg et al., 1994, *Mol. Cell. Endocrinology* 106:111-119), etc.

In a specific embodiment of the invention, liver specific promoter/enhancer sequences may be used to promote the synthesis of PTMs in liver cells for correction of a SERPINA1 defect. Such promoters include, for example, the albumin promoter, transthyretin promoter, CMV promoter, CMV enhancer/chicken beta-actin promoter combination, ApoE promoter, and endogenous SERPINA1 promoter-enhancer elements. In addition, the liver-specific microglobulin promoter cassette optimized for SERPINA1 gene expression may be used, as well as, post-transcriptional elements such as the woodchuck post-transcriptional regulatory element (WPRE).

Any type of plasmid, cosmid, YAC or viral vector can be used to prepare the recombinant DNA construct which can be introduced directly into the tissue site. Alternatively, viral vectors can be used which selectively infect the desired target cell. Vectors for use in the practice of the invention include any eukaryotic expression vectors, including but not limited to viral expression vectors such as those derived from the class of retroviruses, adenoviruses or adeno-associated viruses.

A number of selection systems can also be used, including but not limited to selection for expression of the herpes simplex virus thymidine kinase, hypoxanthine-guanine phosphoribosyltransterase and adenine phosphoribosyl transferase protein in tk-, hgprt- or aprt-deficient cells, respectively. Also, anti-metabolic resistance can be used as the basis of selection for dihydrofolate tranferase (dhfr), which confers resistance to methotrexate; xanthine-guanine phosphoribosyl transferase (gpt), which confers resistance to mycophenolic acid; neomycin (neo), which confers resistance to aminoglycoside G-418; and hygromycin B phosphotransferase (hygro) which confers resistance to hygromycin. In a preferred embodiment of the invention, the cell culture is transformed at a low ratio of vector to cell such that there will be only a single vector, or a limited number of vectors, present in any one cell.

5.3 Uses and Administration of Trans-Splicing Molecules

5.3.1 Use of PTM Molecules for Gene Regulation and Gene Repair

The compositions and methods of the present invention will have a variety of different applications including gene repair of defective SERPINA1 transcripts. For example, targeted trans-splicing, including double-trans-splicing reactions, 3' exon replacement and/or 5' exon replacement can be used to repair or correct SERPINA1 transcripts that are either truncated or contain point mutations. The PTMs of the invention are designed to cleave the targeted SERPINA1 transcript upstream or downstream of a specific mutation or upstream of a premature termination codon and correct the mutant transcript via a trans-splicing reaction which replaces the portion of the transcript containing the mutation with a functional sequence.

In a specific embodiment of the invention, trans-splicing reactions can be used to correct the PI-Z mutation (GAG342AAG) in exon 5 or the less severe PI-S mutation (GAA264GTA) in exon 3, or both mutations. Additionally, the PTMs of the invention may be used to express duplex siRNA molecules directed specifically against mutant SERPINA1 mRNAs. Such duplexed siRNAs are designed to reduce the accumulation of toxic AAT protein in liver cells.

The compositions and methods of the present invention are designed to correct SERPINA1 genetic defects. Specifically, targeted trans-splicing, including double-trans-splicing reactions, 3' exon replacement and/or 5' exon replacement can be used to repair or correct SERPINA1 transcripts that are either truncated or contain point mutations. The PTMs of the invention are designed to bind to a targeted SERPINA1 transcript upstream or downstream of a specific mutation or upstream of a premature termination codon and correct the mutant transcript via a trans-splicing reaction which replaces the portion of the transcript containing the mutation with a functional sequence.

Various delivery systems are known and can be used to transfer the compositions of the invention into cells, e.g. encapsulation in liposomes, microparticles, microcapsules, recombinant cells capable of expressing the composition, receptor-mediated endocytosis (see, e.g., Wu and Wu, 1987, *J. Biol. Chem.* 262:4429-4432), construction of a nucleic acid as part of a retroviral, adenoviral, adeno-associated viral or other vector, injection of DNA, electroporation, calcium phosphate mediated transfection, etc.

The compositions and methods can be used to provide a gene encoding a functional biologically active molecule to cells of an individual with an inherited genetic disorder where expression of the missing or mutant gene product produces a normal phenotype.

Specifically, the compositions and methods can be used to provide sequences encoding a functional biologically active SERPINA1 molecule to cells of an individual with an inherited genetic disorder where expression of the missing or mutant SERPINA1 gene product produces a normal phenotype, i.e., active serine protease inhibition.

In a preferred embodiment, nucleic acids comprising a sequence encoding a PTM are administered to promote PTM function, by way of gene delivery and expression into a host cell. In this embodiment of the invention, the nucleic acid mediates an effect by promoting PTM production. Any of the methods for gene delivery into a host cell available in the art can be used according to the present invention. For general reviews of the methods of gene delivery see Strauss, M. and Barranger, J. A., 1997, Concepts in Gene Therapy, by Walter de Gruyter & Co., Berlin; Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 33:573-596; Mulligan, 1993, *Science* 260:926-932; and Morgan and Anderson, 1993, *Ann. Rev. Biochem.* 62:191-217; 1993, TIBTECH 11 (5):155-215. Exemplary methods are described below.

Delivery of the PTM into a host cell may be either direct, in which case the host is directly exposed to the PTM or PTM encoding nucleic acid molecule, or indirect, in which case, host cells are first transformed with the PTM or PTM encoding nucleic acid molecule in vitro, then transplanted into the host. These two approaches are known, respectively, as in vivo or ex vivo gene delivery.

In a specific embodiment, the nucleic acid is directly administered in vivo, where it is expressed to produce the PTM. This can be accomplished by any of numerous methods known in the art, e.g., by constructing it as part of an appropriate nucleic acid expression vector and administering it so that it becomes intracellular, e.g. by infection using a defective or attenuated retroviral or other viral vector (see U.S. Pat. No. 4,980,286), or by direct injection of naked DNA, or by use of microparticle bombardment (e.g., a gene gun; Biolistic, Dupont, Bio-Rad), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, *J. Biol. Chem.* 262:4429-4432).

In a specific embodiment, a viral vector that contains the PTM can be used. For example, a retroviral vector can be utilized that has been modified to delete retroviral sequences that are not necessary for packaging of the viral genome and integration into host cell DNA (see Miller et al., 1993, *Meth. Enzymol.* 217:581-599). Alternatively, adenoviral or adeno-associated viral vectors can be used for gene delivery to cells or tissues. (See, Kozarsky and Wilson, 1993, *Current Opinion in Genetics and Development* 3:499-503 for a review of adenovirus-based gene delivery).

In a preferred embodiment of the invention an adeno-associated viral vector may be used to deliver nucleic acid molecules capable of encoding the PTM. The vector is designed so that, depending on the level of expression desired, the promoter and/or enhancer element of choice may be inserted into the vector.

Another approach to gene delivery into a cell involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. The resulting recombinant cells can be delivered to a host by various methods known in the art. In a preferred embodiment, the cell used for gene delivery is autologous to the host's cell.

In a specific embodiment of the invention, hepatic stem cells, oval cells, or hepatocytes may be removed from a subject having AAT and transfected with a nucleic acid molecule capable of encoding a PTM designed to correct a SERPINA1 genetic disorder. Cells may be further selected, using routine methods known to those of skill in the art, for integration of the nucleic acid molecule into the genome thereby providing a stable cell line expressing the PTM of interest. Such cells are then transplanted into the subject thereby providing a source of normal SERPINA1 protein.

The present invention also provides for pharmaceutical compositions comprising an effective amount of a PTM or a nucleic acid encoding a PTM, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

In specific embodiments, pharmaceutical compositions are administered: in diseases or disorders involving an absence or decreased (relative to normal or desired) level of SERPINA1 protein or function, for example, in hosts where the protein is lacking, genetically defective, biologically inactive or underactive, or under expressed. The activity of the normal protein encoded for by the chimeric mRNA resulting from the PTM mediated trans-splicing reaction can be readily detected, e.g., by obtaining a host tissue sample (e.g., from biopsy tissue) and assaying it in vitro for mRNA or protein levels, structure and/or activity of the expressed chimeric mRNA.

In specific embodiments, pharmaceutical compositions are administered in diseases or disorders involving an absence or decreased (relative to normal or desired) level of an endogenous SERPINA1 protein or function, for example, in hosts where the SERPINA1 protein is lacking, genetically defective, biologically inactive or underactive, or under expressed. Such disorders include but are not limited to AAT deficiency. The activity of the SERPINA1 protein encoded for by the chimeric or composite mRNA resulting from the PTM mediated trans-splicing reaction can be readily detected, e.g., by obtaining a host tissue sample (e.g., from biopsy tissue) and assaying it in vitro for mRNA or protein levels, structure and/or activity of the expressed chimeric mRNA.

Many methods standard in the art can be thus employed, including but not limited to immunoassays to detect and/or visualize the protein encoded for by the chimeric mRNA (e.g., Western blot, immunoprecipitation followed by sodium dodecyl sulfate polyacrylamide gel electrophoresis, immunocytochemistry, etc.) and/or hybridization assays to detect formation of chimeric mRNA expression by detecting and/or visualizing the presence of chimeric mRNA (e.g., Northern assays, dot blots, in situ hybridization, and Reverse-Transcription PCR, etc.), etc.

In a specific embodiment, it may be desirable to administer the pharmaceutical compositions of the invention locally to the area in need of treatment, i.e., liver tissue. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, hydrogels.

The PTM will be administered in amounts which are effective to produce the desired effect in the targeted cell. Effective dosages of the PTMs can be determined through procedures well known to those in the art which address such parameters as biological half-life, bioavailability and toxicity. The amount of the composition of the invention which will be effective will depend on the severity of the AAT deficiency being treated, and can be determined by standard clinical techniques. Such techniques include analysis of blood samples to determine levels of circulating AAT protein. In addition, in vitro assays may optionally be employed to help identify optimal dosage ranges.

The present invention also provides a pharmaceutical pack or kit comprising one or more containers filled with one or more of the ingredients of the pharmaceutical compositions of the invention optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

Correction of Serpin A1 Gene Using PTMS

To demonstrate conversion of the PI-Z (GAG342AAG in SERPIN A1) variant to the PI-M "corrected" form of human SERPINA1 in an in vitro model system, the following study was undertaken. A high throughput screen, such as the one described in patent application Ser. No. 10/693,192, was utilized to identify PTM binding domains capable of efficient trans-splicing to the desired target (human SERPIN A1 intron 2). Briefly, a hemi green fluorescent protein (GFP)-SERPINA1 mini-gene target (FIG. 5B) comprised of the N-terminal portion (nucleotides 1-209) of Zoanthus GFP followed by sequences from the human SERPINA1 gene (the first nucleotide of intron 2 through the terminal nucleotide of exon 3) was constructed and cloned into a recombinant vector. A corresponding PTM binding domain library specific for SERPINA1 intron 2 (FIG. 5A) was constructed by sonication of a PCR product comprised of a segment (the terminal 42 nucleotides) of exon 2 through a segment (the initial 74 nucleotides) of exon 3, including intron 2 in its entirety. Binding domain fragments ranging in size from 50-300 nucleotides were cloned upstream of a trans-splicing domain (consisting of a short spacer region, branch point sequence, polypyrimidine tract and acceptor AG) in a PTM vector containing the C terminal (nucleotides 210-696) portion of GFP.

Approximately one million PTMs (binding domains) were delivered clonally by protoplast fusion to a mammalian cell line (Cos7) which had been transfected with the GFP-SER-PIN A1 mini-gene target 24 hours prior. After a 48 hour incubation, cells were analyzed for GFP expression using FACS (FIG. 5C). Trans-splicing between the mini-gene target and individual PTMs results in the reconstitution and expression of full length GFP (FIGS. 5B and 5C, top). Neither the mini-gene target nor the PTM library by itself is capable of GFP expression (FIG. 5C, bottom). GFP positive cells were collected from two fractions: high and low green (representing 0.017% and 0.029%, respectively, of the total number of cells (30 million) analyzed, FIG. 5C). DNA was extracted from each fraction and transformed into bacterial cells for the isolation and further characterization of individual lead PTMs. Approximately 92% of PTMs characterized from each fraction contained at least one binding domain.

Individual DNA samples from 175 lead PTMs from each fraction were transfected into a mammalian cell line (293T) containing integrated copies of the GFP-SERPINA1 mini-gene target. Cells were analyzed for GFP expression as detailed above (representative histograms are shown in FIG. 6B). Samples which scored positive for GFP expression in the presence of the integrated (low copy) target (17.9% and 12.0% of the individual lead PTMs analyzed from the high and low green fractions, respectively) were sequenced and further characterized for cryptic cis-splicing of the PTM as follows. Total RNA was isolated from cells transfected with a GFP-based lead PTM and the binding domain was amplified by RT-PCR as illustrated in FIG. 9A. Resulting product sizes were compared with products amplified from the corresponding plasmid DNA. Minimal cryptic cis-splicing was observed for all lead PTMs analyzed.

Sequence alignment of the lead binding domains with intron 2 of SERPIN A1 revealed a significant distribution of sequences toward the 5' half of the intron (examples are shown in FIG. 6A). Additionally, many PTMs contained binding domains with defined sequence gaps, reflecting the complexity of the initial PTM binding domain library.

Figure 7:
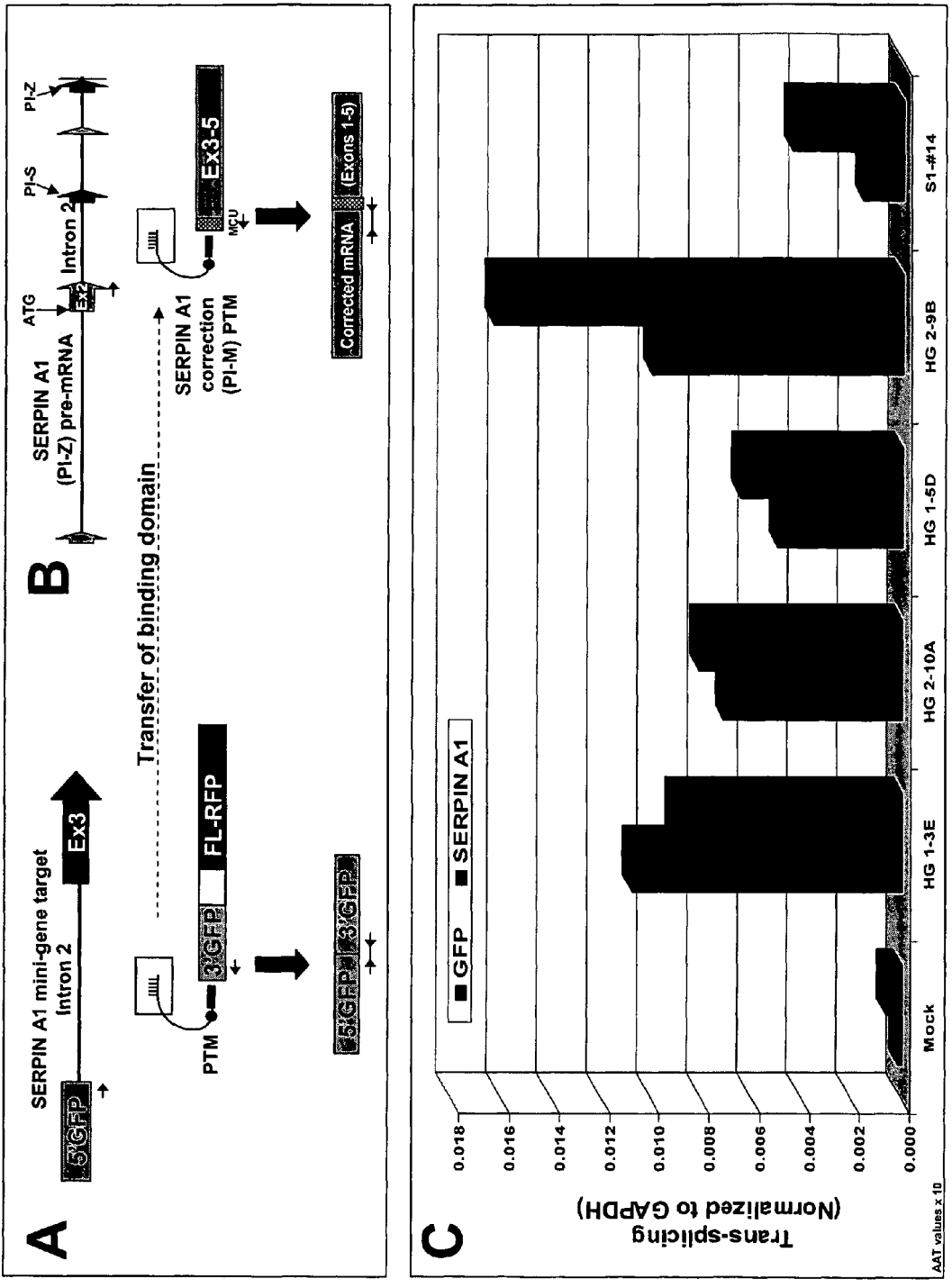
Figure 8:
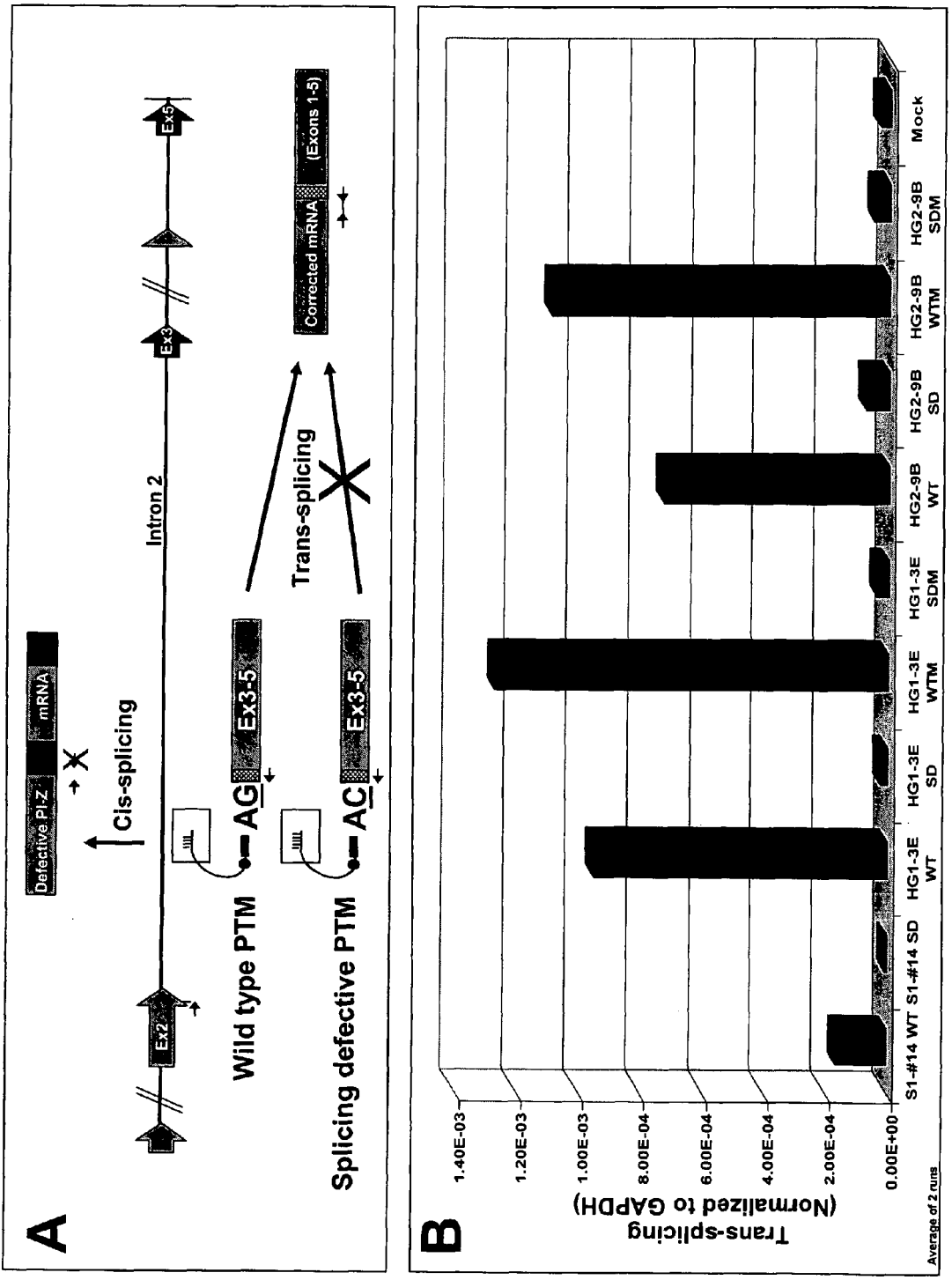

The level or efficiency of trans-splicing was quantified using qRT-PCR analysis of total RNA isolated from each sample. Based on this analysis (FIG. 7C) four of the most efficient (HG1-3E, HG2-10A, HG1-5D and HG2-9B, listed below in Table 1) and one "average" (S1-#14) binding domain were transferred into a vector containing a PTM specifically designed to trans-splice to and correct the defective human SERPIN A1 target (FIG. 7). This correction-based PTM is comprised of a lead binding domain followed by a trans-splicing domain followed by exons 3 through 5 of the SERPIN A1 PI-M gene that will replace the defective exon(s) of the PI-Z variant of the human SERPIN A1 gene. Exon 3 of all SERPIN A1 correction PTM constructs contains modified codons to allow for discrimination by qRT-PCR of corrected (PI-M) RNA products from endogenous (PI-Z) or contaminating products. Matched human SERPIN A1-based PTM controls in which the 3' splice acceptor AG sequence was modified to AC to disrupt splicing potential at this site were also constructed for in vitro comparison with their wild type counterparts (FIG. 8).

TABLE 1

Human SERPINA1 Lead Binding Domain Sequences

HG1-3E: (SEQ ID NO: 11)
5'-TATTCTACATATACAGTATACACAAGGACATTAAAGGCTCTGAAAAG
TTCTGCAGAGCTGTCAGTAGTTTTGACAGTTTAATCTATTATTTCCTCAA

TABLE 1-continued

Human SERPINA1 Lead Binding Domain Sequences

ATTACTCAATGATGGAAAACATTTTAGTGTTTGTGTGTAGAAAACTGAAG
AATCCACGCTGAAAAGCATTGCTATGGCCCATAATGCATT-3'

HG2-10A: (SEQ ID NO: 12)
5'-AATGCATTGTTTTTGTCAAAAGCTAATTGTGTTAGAGGCAGGATTTG
AACCCAGGTCTTTCAGATTGCAAAACTGATACTGATTTTTGTTCTATAGT
TCTAAGCATTATATATTCTACATATACAGTATACACAAGGACATTAAAGG
CTCTGAAAAGTTCTGCAGAGCTGTCAGTAGTTTTGACAGTTTAATCTATT
ATTTCCTCAAATTACTCAATGATGGAAAAC-3'

HG1-5D: (SEQ ID NO: 13)
5'-TTCCATGAAACTATCCCTTTATGCAGTGTATTACAATTTGTTCTATA
GTTCTAAGCATTATATATTCTACATATACAGTATACACAAGGACATTAAA
GGCTCTGAAAAGTTCTGCAGAGCTGTCAGTAGTTTTGACAGTTTAATCTA
TTATTTCCTCAAATTACTCAA-3'

HG2-9B: (SEQ ID NO: 14)
5'-TCCCAGCTTTCTCATTGGACAGAAGGAGGAGACTGGGGCTGGAGAGG
GACCTGGGCCCCCACTAAGGCCACAGCAGACGCAGGACTTTAGCTGTGCT
GACTGCAGCCTGGCTGCTCTCCACTGCCCTGTAGAATGCATTGTTTTTGT
CAAAAGCTAATTGTGTTAGAGGCAGGATTTGAACCCAGGTCTTTCAGATT
GCAAAACTGATACTGATTCTGGGACACTAGAGTCGTGTAAAGTATGCTCC
ATGAAACTATCCCTTTATGCAGTGTATTACAATTTGTTCTATAGTTCTA
A-3'

S1-#14: (SEQ ID NO: 15)
5'-CTATGCTGTTTTCCTGGGACAGTGGGAGCTGGCTTAGAATGCCCTGG
GGCCCCCAGGACCCTAGCATTTTAACCCCTCAGGGGCAGGAAGGCAG-3'

Figure 9:
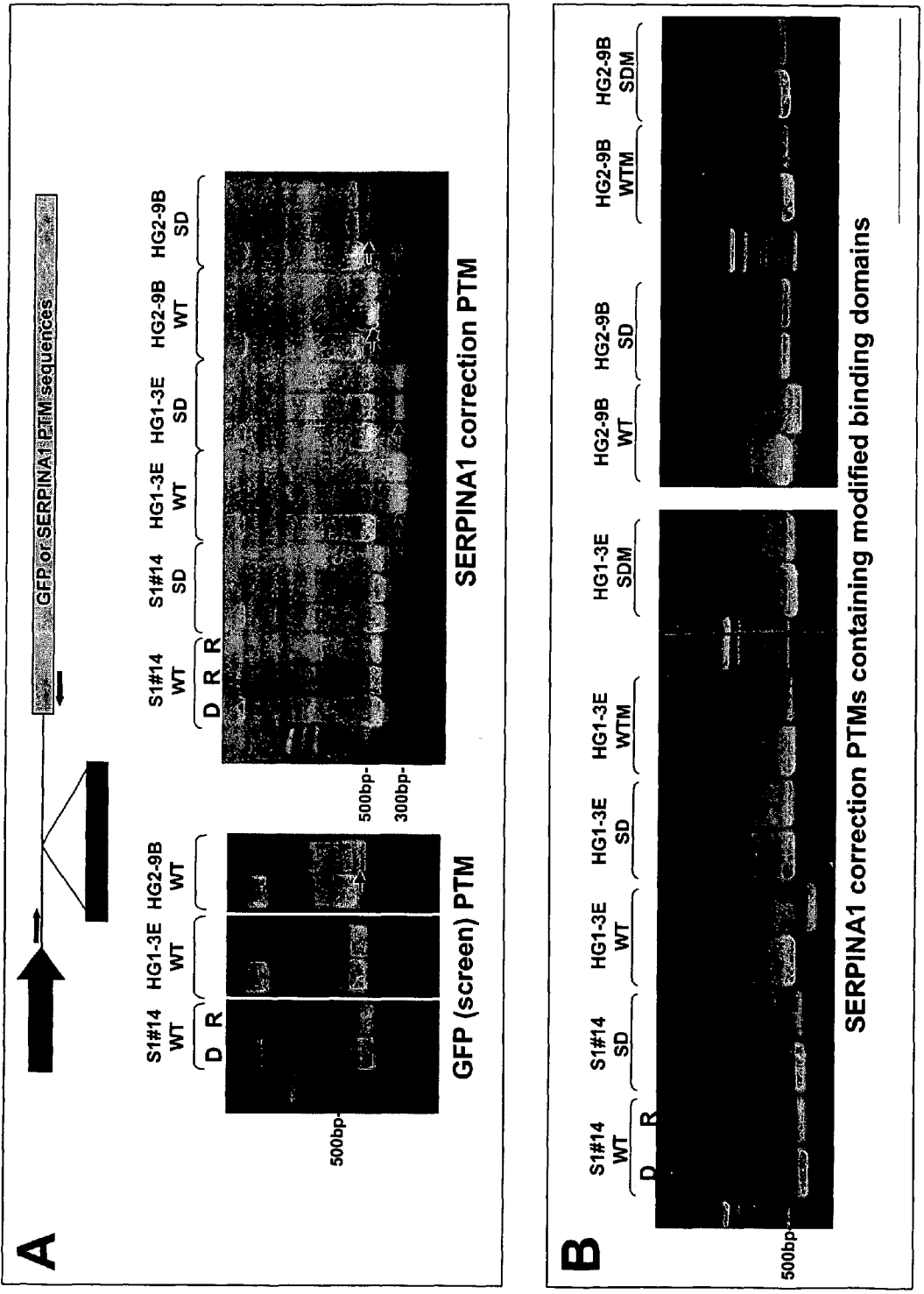

The selected lead PTMs were analyzed for SERPINA1 correction by transfection into a Hepa1-6 mouse hepatoma cell line carrying integrated copies of the defective human SERPINA1 PI-Z genomic sequence (~11 kb containing all exonic (1-5) and intronic (1-4) sequences). Human SERPINA1 expression in the Hepa1-6 cell line was verified by Western and IEF blotting using antibodies specific for SERPINA1. 48 hours post-transfection, total RNA was isolated from each sample for qRT-PCR analysis (FIGS. 7C and 8B). To assess cryptic cis-splicing of the PTM, the binding domains were amplified by RT-PCR from total RNA from transfected samples as illustrated in FIG. 9. Resulting product sizes were compared with products amplified from the corresponding plasmid DNA. All binding domains in the correction PTM context exhibited significantly more cryptic cis-splicing (FIG. 9A) compared to the matched GFP PTMs. This difference is also reflected in the variability in the level of trans-splicing (by qRT-PCR) observed between samples (see HG1-3E and HG2-9B, FIG. 7C).

Sequences were modified to eliminate potential cryptic splice sites and trans-splicing efficiency was reassessed (FIGS. 8B and 9B). The most efficient lead PTMs (HG1-3E and HG2-9B) trans-spliced approximately 4-7 fold more efficiently than an "average" PTM (S1-#14) targeting the same intron. To validate that the level of trans-splicing observed was due to the activity of the PTM, trans-splicing was assessed in the matched splicing defective PTMs. Compared to their wild type counterparts, trans-splicing dramatically decreased from 10 to 40 fold. Thus these results illustrate that trans-splicing through the use of targeted functional PTMs can be used as a mechanism to provide for the correction of a defective SERPIN A1 RNA in vitro.

7. EXAMPLE

Correction of Serpin A1 Gene Using PTMS Using a Transgenic Mouse

Conversion of the PI-Z variant to the PI-M "corrected" form of human SERPINA1 can be demonstrated in vivo in a transgenic "knock-in" mouse model (herein referred to as hAAT/PI-Z) containing integrated copies of the human SERPINA1 PI-Z gene (Sifers, R. N. et al., Tissue Specific Expression of the Human Alpha1-Antitrypsin Gene in Transgenic Mice. 1987, Nucleic Acids Res. 15(4): 1459-1475; Carlson, J. A. et al., Accumulation of PiZ alpha1-Antitrypsin Causes Liver Damage in Transgenic Mice. 1989, J. Clin. Invest. 83:1183-1190). Expression and efficient secretion of the native mouse SERPINA1 gene products protects the hAAT/PI-Z mouse lung from injury, however, expression of the human SERPINA1 PI-Z variant results in the accumulation of the mis-folded protein in the endoplasmic reticulum of hepatocytes (e.g. formation of periodic-acid Schiff (PAS)-positive staining globules), leading to hepatocellular proliferation and chronic liver injury thus recapitulating the human liver disease state (Geller, S. A. et al. Hepatocarcinogenesis is the sequel to hepatitis in Z#2 alpha 1-antitrypsin transgenic mice: Histopathological and DNA ploidy studies. 1994, Hepatology 19:389-397). Delivery of a human SERPINA1-targeted PTM to the liver and the corresponding trans-splicing reaction results in the correction of the defective exon(s) and leads to the expression and secretion of the corrected PI-M form of SERPINA1. Concomitantly, the expression and hepatocellular accumulation of the toxic PI-Z variant of the protein are reduced, thereby reducing the degree of liver injury.

Delivery of the lead PTM (binding domain, trans-splicing domain and corrected forms of SERPINA1 exons 3-5) into the hAAT/PI-Z mouse model is achieved either by hydrodynamic delivery of naked DNA (minicircle) molecules via the tail vein (Chen, Z. Y. et al., 2003, Mol. Ther. 8(3):495-500; Zhang, G. et al., 2003, Gene Therapy 11:675-682), through transduction using a recombinant adeno-associated virus (rAAV), or through an alternative delivery method (e.g. other viral vectors, lipid or polymer-based nanoparticles, etc [see para 0087]). For viral (AAV) delivery, the PTM is packaged into rAAV corresponding to an optimal serotype and the resulting virus is directly administered intraportally into young hAAT/PI-Z mice. Treated animals are tracked for ten (10) to twenty six (26) weeks post-injection. Blood samples are collected at regular intervals to monitor levels of human SERPINA1 expression by serum chemistry analysis, ELISA, Western blotting or isoelectric focusing (phenotyping) using antibodies specific for SERPINA1. Conversion of the PI-Z to PI-M protein variant results in the increased secretion of SERPINA1 (PI-M) into the serum. A 20% increase in secreted levels of the human SERPINA1 is readily detectable by blood chemistry analysis and is suggestive of a therapeutic (>0.9 mg/ml) response. Variations in the levels of specific transaminases (e.g. alanine and aspartate aminotransferases), which function as indirect indicators of alterations in the injured liver state, are also monitored via blood chemistry analysis.

Animals are sacrificed at pre-determined post-injection end-points (10 to 26 weeks) for tissue histology, immunohistochemistry, serum biochemistry and molecular (RT-qPCR) analysis. Liver sections are stained for 1) the presence/frequency of PAS-positive globules and 2) the level of hepatocyte proliferation and turnover using BrdU. Decreases in both the frequency of PAS-positive globules and the level of hepatocyte turnover are indicative of PTM-based conversion from the PI-Z to PI-M variant. Changes in the morphology of the ER due to reduced accumulation of the PI-Z protein are also visible by electron microscopy. The degree of conversion (trans-splicing) is assessed at the RNA level by qRT-PCR analysis of hepatic RNA.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosures of which are incorporated by reference in their entireties.

We claim:

1. An isolated liver cell comprising a nucleic acid molecule wherein said nucleic acid molecule comprises:
   a) one or more target binding domains that target binding of the nucleic acid molecule to a defective exon of a SERPINA1 pre-mRNA expressed from an endogenous defective SERPINA1 sequence within the cell;
   b) a 3' splice region comprising a branch point and a 3' splice acceptor site;
   c) a spacer region that separates the 3' splice region from the target binding domain;
   d) a nucleotide sequence to be trans-spliced to the target pre-mRNA wherein said nucleotide sequence encodes a corrective SERPINA1 exon which forms a chimeric nucleic acid molecule with endogenous SERPINA1 pre-mRNA, wherein upon trans-splicing, a corrected mRNA is formed; and
   e) a Tia-1 binding sequence within 100 nucleotides of a 5' donor site,
   wherein said nucleic acid molecule is recognized by nuclear splicing components within the cell, and wherein a defective exon of the endogenous SERPINA1 pre-mRNA is replaced.

2. An isolated liver cell comprising a nucleic acid molecule wherein said nucleic acid molecule comprises:
   a) one or more target binding domains that target binding of the nucleic acid molecule to a defective exon of a SERPINA1 pre-mRNA expressed from an endogenous defective SERPINA1 sequence within the cell;
   b) a 3' splice acceptor site;
   c) a spacer region that separates the 3' splice region from the target binding domain;
   d) a nucleotide sequence to be trans-spliced to the target pre-mRNA wherein said nucleotide sequence encodes a corrective SERPINA1 exon which forms a chimeric nucleic acid molecule with endogenous SERPINA1 pre-mRNA, wherein upon trans-splicing, a corrected mRNA is formed; and
   e) a Tia-1 binding sequence within 100 nucleotides of a 5' donor site,
   wherein said nucleic acid molecule is recognized by nuclear splicing components within the cell, and wherein a defective exon of the endogenous SERPINA1 pre-mRNA is replaced.

3. An isolated liver cell comprising a nucleic acid molecule wherein said nucleic acid molecule comprises:
   a) one or more target binding domains that target binding of the nucleic acid molecule to a defective exon of a SERPINA1 pre-mRNA expressed from an endogenous defective SERPINA1 sequence within the cell;
   b) a 5' splice site;
   c) a spacer region that separates the 5' splice site from the target binding domain;
   d) a nucleotide sequence to be trans-spliced to the target pre-mRNA wherein said nucleotide sequence encodes a corrective SERPINA1 exon which forms a chimeric nucleic acid molecule with endogenous SERPINA1 pre-mRNA, wherein upon trans-splicing, a corrected mRNA is formed; and e) a Tia-1 binding sequence within 100 nucleotides of a 5' donor site, wherein said nucleic acid molecule is recognized by nuclear splicing components within the cell, and wherein a defective exon of the endogenous SERPINA1 pre-mRNA is replaced.

4. The isolated liver cell of claim 1 wherein the 3' splice region further comprises a pyrimidine tract.

5. The isolated liver cell of claim 3 wherein said nucleic acid molecule further comprises a safety sequence comprising one or more complementary sequences that bind to one or both sides of the 5' splice site.

6. An isolated liver cell comprising a nucleic acid molecule wherein said nucleic acid molecule comprises:
   a) one or more target binding domains that target binding of the nucleic acid molecule to
   a defective exon of a SERPINA1 pre-mRNA expressed from an endogenous defective SERPINA1 sequence within the cell;
   b) a 3' splice region comprising a branch point and a 3' splice acceptor site;
   c) a spacer region that separates the 3' splice region from the target binding domain;
   d) a nucleotide sequence to be trans-spliced to the target pre-mRNA wherein said
   nucleotide sequence encodes a corrective SERPINA1 exon which forms a chimeric nucleic acid molecule with endogenous SERPINA1 pre-mRNA, wherein upon trans-splicing, a corrected mRNA is formed; and
   e) a Tia-1 binding sequence within 100 nucleotides of a 5' donor site, wherein said nucleic acid molecule is recognized by nuclear splicing components within the cell, and wherein a defective exon of the endogenous SERPINA1 pre-mRNA is replaced, and wherein the nucleic acid molecule further comprises nucleotide sequence encoding a siRNA which binds to a mutant SERPINA1 transcript, and not to a SERPINA1 sequence encoding a normal protein.

7. An isolated liver cell comprising a recombinant vector wherein said vector expresses a nucleic acid molecule comprising:
   a) one or more target binding domains that target binding of the nucleic acid molecule to
   a defective exon of a SERPINA1 pre-mRNA expressed from an endogenous defective SERPINA1 sequence within the cell;
   b) a 3' splice region comprising a branch point and a 3' splice acceptor site;
   c) a spacer region that separates the 3' splice region from the target binding domain;
   d) a nucleotide sequence to be trans-spliced to the target pre-mRNA wherein said
   nucleotide sequence encodes a corrective SERPINA1 exon which forms a chimeric nucleic acid molecule with endogenous SERPINA1 pre-mRNA, wherein upon trans-splicing, a corrected mRNA is formed; and
   e) a Tia-1 binding sequence within 100 nucleotides of a 5' donor site, wherein said nucleic acid molecule is recognized by nuclear splicing components within the cell, and wherein a defective exon of said endogenous SERPINA1 pre-mRNA is replaced.

8. An isolated liver cell comprising a recombinant vector wherein said vector expresses a nucleic acid molecule comprising:
   a) one or more target binding domains that target binding of the nucleic acid molecule to
   a defective exon of a SERPINA1 pre-mRNA expressed from an endogenous defective SERPINA1 sequence within the cell;
   b) a 3' splice acceptor site;
   c) a spacer region that separates the 3' splice region from the target binding domain; and
   d) a nucleotide sequence to be trans-spliced to the target pre-mRNA wherein said
   nucleotide sequence encodes a corrective SERPINA1 exon which forms a chimeric nucleic acid molecule with endogenous SERPINA1 pre-mRNA, wherein upon trans-splicing, a corrected mRNA is formed; and
   e) a Tia-1 binding sequence within 100 nucleotides of a 5' donor site, wherein said nucleic acid molecule is recognized by nuclear splicing components within the cell, and wherein a defective exon of said endogenous SERPINA1 pre-mRNA is replaced.

9. An isolated liver cell comprising a recombinant vector wherein said vector expresses a nucleic acid molecule comprising:
   a) one or more target binding domains that target binding of the nucleic acid molecule to
   a defective exon of a SERPINA1 pre-mRNA expressed from an endogenous defective SERPINA1 sequence within the cell;
   b) a 5' splice site;
   c) a spacer region that separates the 5' splice site from the target binding domain;
   d) a nucleotide sequence to be trans-spliced to the target pre-mRNA wherein said
   nucleotide sequence encodes a corrective SERPINA1 exon which forms a chimeric nucleic acid molecule with endogenous SERPINA1 pre-mRNA, wherein upon trans-splicing, a corrected mRNA is formed; and
   e) a Tia-1 binding sequence within 100 nucleotides of a 5' donor site, wherein said nucleic acid molecule is recognized by nuclear splicing components within the cell, and wherein defective exon of said endogenous SERPINA1 pre-mRNA is replaced.

10. The isolated liver cell of claim 7 wherein the 3' splice region further comprises a pyrimidine tract.

11. The isolated liver cell of claim 7 or 8 wherein the nucleic acid molecule further comprises a safety nucleotide sequence comprising one or more complementary sequences that bind to one or more sides of the 3' splice region.

12. An isolated cell comprising a recombinant vector wherein said vector expresses a nucleic acid molecule comprising:
   a) one or more target binding domains that target binding of the nucleic acid molecule to
   a defective exon of a SERPINA1 pre-mRNA expressed from an endogenous defective SERPINA1 sequence within the cell;
   b) a 3' splice region comprising a branch point and a 3' splice acceptor site;
   c) a spacer region that separates the 3' splice region from the target binding domain;
   d) a nucleotide sequence to be trans-spliced to the target pre-mRNA wherein said
   nucleotide sequence encodes a corrective SERPINA1 exon which forms a chimeric nucleic acid molecule with endogenous SERPINA1 pre-mRNA, wherein upon trans-splicing, a corrected mRNA is formed; and
   e) a Tia-1 binding sequence within 100 nucleotides of a 5' donor site, wherein said nucleic acid molecule is recognized by nuclear splicing components within the cell, and wherein a defective exon of said endogenous SERPINA1 pre-mRNA is replaced, and
wherein the nucleic acid molecule further comprises a nucleotide sequence capable encoding a siRNA which binds to a mutant SERPINA1 transcript, and not to a SERPINA1 sequence encoding a normal protein.

13. A nucleic acid molecule comprising:
a) one or more target binding domains that target binding of the nucleic acid molecule to
a defective exon of a SERPINA1 pre-mRNA expressed from an endogenous defective SERPINA1 sequence within an isolated liver cell;
b) a 3' splice region comprising a branch point and a 3' splice acceptor site;
c) a spacer region that separates the 3' splice region from the target binding domain;
d) a nucleotide sequence to be trans-spliced to the target pre-mRNA wherein said
nucleotide sequence encodes a corrective SERPINA1 exon which forms a chimeric nucleic acid molecule with endogenous SERPINA1 pre-mRNA, wherein upon trans-splicing, a corrected mRNA is formed; and
e) a Tia-1 binding sequence within 100 nucleotides of a 5' donor site,
wherein said nucleic acid molecule is recognized by nuclear splicing components within the cell, and wherein a defective exon of said endogenous SERPINA1 pre-mRNA is replaced.

14. A nucleic acid molecule comprising:
a) one or more target binding domains that target binding of the nucleic acid molecule to
a defective exon of a SERPINA1 pre-mRNA expressed from an endogenous defective SERPINA1 sequence within an isolated liver cell;
b) a 3' splice acceptor site;
c) a spacer region that separates the 3' splice region from the target binding domain;
d) a nucleotide sequence to be trans-spliced to the target pre-mRNA wherein said
nucleotide sequence encodes a corrective SERPINA1 exon which forms a chimeric nucleic acid molecule with endogenous SERPINA1 pre-mRNA, wherein upon trans-splicing, a corrected mRNA is formed; and
e) a Tia-1 binding sequence within 100 nucleotides of a 5' donor site,
wherein said nucleic acid molecule is recognized by nuclear splicing components within the cell, and wherein a defective exon of said endogenous SERPINA1 pre-mRNA is replaced.

15. A nucleic acid molecule comprising:
a) one or more target binding domains that target binding of the nucleic acid molecule to
a defective exon of a SERPINA1 pre-mRNA expressed within an isolated cell;
b) a 5' splice site;
c) a spacer region that separates the 5' splice site from the target binding domain; and
d) a nucleotide sequence to be trans-spliced to the target pre-mRNA wherein said
nucleotide sequence encodes a corrective SERPINA1 exon which forms a chimeric nucleic acid molecule with endogenous SERPINA1 pre-mRNA, wherein upon trans-splicing, a corrected mRNA is formed; and
e) a Tia-1 binding sequence within 100 nucleotides of a 5' donor site,
wherein said nucleic acid molecule is recognized by nuclear splicing components within the cell.

16. The nucleic acid molecule of claim 13 wherein the 3' splice region further comprises a pyrimidine tract.

17. The nucleic acid molecule of claim 13 or 14 wherein the nucleic acid molecule further comprises a safety nucleotide sequence comprising one or more complementary sequences that bind to one or more sides of the 3' splice region.

18. A nucleic acid molecule comprising:
a) one or more target binding domains that target binding of the nucleic acid molecule to
a defective exon of a SERPINA1 pre-mRNA expressed from an endogenous defective SERPINA1 sequence within an isolated liver cell;
b) a 3' splice region comprising a branch point and a 3' splice acceptor site;
c) a spacer region that separates the 3' splice region from the target binding domain;
d) a nucleotide sequence to be trans-spliced to the target pre-mRNA wherein said
nucleotide sequence encodes a corrective SERPINA1 exon which forms a chimeric nucleic acid molecule with endogenous SERPINA1 pre-mRNA, wherein upon trans-splicing, a corrected mRNA is formed; and
e) a Tia-1 binding sequence within 100 nucleotides of a 5' donor site,
wherein said nucleic acid molecule is recognized by nuclear splicing components within the cell, and wherein a defective exon of said endogenous SERPINA1 pre-mRNA is replaced, and wherein the nucleic acid molecule further comprises a nucleotide sequence capable encoding a siRNA capable of binding to a mutant SERPINA1 transcript.

19. A eukaryotic expression viral vector wherein said vector expresses a nucleic acid molecule comprising:
a) one or more target binding domains that target binding of the nucleic acid molecule to
a defective exon of a SERPINA1 pre-mRNA expressed from an endogenous defective SERPINA1 sequence within an isolated liver cell;
b) a 3' splice region comprising a branch point and a 3' splice acceptor site;
c) a spacer region that separates the 3' splice region from the target binding domain;
d) a nucleotide sequence to be trans-spliced to the target pre-mRNA wherein said
nucleotide sequence encodes a corrective SERPINA1 exon which forms a chimeric nucleic acid molecule with endogenous SERPINA1 pre-mRNA, wherein upon trans-splicing, a corrected mRNA is formed; and
e) a Tia-1 binding sequence within 100 nucleotides of a 5' donor site,
wherein said nucleic acid molecule is recognized by nuclear splicing components within the cell and wherein expression of the nucleic acid molecule is controlled by a liver cell specific promoter, and wherein a defective exon of said endogenous SERPINA1 pre-mRNA is replaced.

20. A eukaryotic expression viral vector wherein said vector expresses a nucleic acid molecule comprising:
a) one or more target binding domains that target binding of the nucleic acid molecule to
a defective exon of a SERPINA1 pre-mRNA expressed from an endogenous defective SERPINA1 sequence within an isolated liver cell;
b) a 3' splice acceptor site;
c) a spacer region that separates the 3' splice region from the target binding domain;
d) a nucleotide sequence to be trans-spliced to the target pre-mRNA wherein said nucleotide sequence encodes a corrective SERPINA1 exon which forms a chimeric nucleic acid molecule with endogenous SERPINA1 pre-mRNA, wherein upon trans-splicing, a corrected mRNA is formed; and e) a Tia-1 binding sequence within 100 nucleotides of a 5' donor site, wherein said nucleic acid molecule is recognized by nuclear splicing components within the cell and wherein expression of the nucleic acid molecule is controlled by a liver cell specific promoter, and wherein a defective exon of the endogenous SERPINA1 pre-mRNA is replaced.

21. A eukaryotic expression viral vector wherein said vector expresses a nucleic acid molecule comprising:
a) one or more target binding domains that target binding of the nucleic acid molecule to
a defective exon of a SERPINA1 pre-mRNA expressed from an endogenous defective SERPINA1 sequence within an isolated liver cell;
b) a 5' splice site;
c) a spacer region that separates the 5' splice site from the target binding domain;
d) a nucleotide sequence to be trans-spliced to the target pre-mRNA wherein said
nucleotide sequence encodes a corrective SERPINA1 exon which forms a chimeric nucleic acid molecule with endogenous SERPINA1 pre-mRNA, wherein upon trans-splicing, a corrected mRNA is formed; and
e) a Tia-1 binding sequence within 100 nucleotides of a 5' donor site,
wherein said nucleic acid molecule is recognized by nuclear splicing components within the cell and wherein expression of the nucleic acid molecule is controlled by a liver cell specific promoter, and wherein a defective exon of the endogenous SERPINA1 pre-mRNA is replaced.

22. The viral vector of claim 19 wherein the nucleic acid molecule further comprises a pyrimidine tract.

23. The viral vector of claim 19 or 20 wherein the nucleic acid molecule further comprises a safety nucleotide sequence comprising one or more complementary sequences that bind to one or more sides of the 3' splice region.

24. A viral vector of wherein said vector expresses a nucleic acid molecule comprising:
a) one or more target binding domains that target binding of the nucleic acid molecule to
a defective exon of a SERPINA1 pre-mRNA expressed from an endogenous defective SERPINA1 sequence within an isolated liver cell;
b) a 3' splice region comprising a branch point and a 3' splice acceptor site;
c) a spacer region that separates the 3' splice region from the target binding domain;
d) a nucleotide sequence to be trans-spliced to the target pre-mRNA wherein said
nucleotide sequence encodes a corrective SERPINA1 exon which forms a chimeric nucleic acid molecule with endogenous SERPINA1 pre-mRNA, wherein upon trans-splicing, a corrected mRNA is formed; and
e) a Tia-1 binding sequence within 100 nucleotides of a 5' donor site,
wherein said nucleic acid molecule is recognized by nuclear splicing components within the cell and wherein expression of the nucleic acid molecule is controlled by a liver cell specific promoter, and wherein a defective exon of said endogenous SERPINA1 pre-mRNA is replaced, and wherein the nucleic acid molecule further comprises a nucleotide sequence capable encoding a siRNA capable of binding to a mutant SERPINA1 transcript.

* * * * *